US009074231B2

(12) United States Patent
Zhu

(10) Patent No.: US 9,074,231 B2
(45) Date of Patent: Jul. 7, 2015

(54) REDUCING NON-SPECIFIC ENZYME BINDING TO ENHANCE LIGNOCELLULOSE CONVERSION

(71) Applicant: The United States of America as Represented by the Secretary of Agriculture, Washington, DC (US)

(72) Inventor: JunYong Zhu, Madison, WI (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 12 days.

(21) Appl. No.: 13/652,267

(22) Filed: Oct. 15, 2012

(65) Prior Publication Data

US 2014/0106407 A1    Apr. 17, 2014

(51) Int. Cl.
    *C12P 19/02* (2006.01)
    *C12P 7/10* (2006.01)
    *C12P 19/14* (2006.01)

(52) U.S. Cl.
    CPC ............ *C12P 19/14* (2013.01); *Y02E 50/343* (2013.01); *C12P 19/02* (2013.01); *C12P 7/10* (2013.01); *C12P 2201/00* (2013.01); *Y02E 50/16* (2013.01)

(58) Field of Classification Search
    USPC .......... 435/209, 99, 165, 252.3, 277, 161, 14, 435/162, 163, 170, 173.2, 183, 278; 536/23.2; 162/77
    See application file for complete search history.

(56) References Cited

PUBLICATIONS

Kansoh et al (Biodegradation and utilization of bagasse with Trichoderma reesie. Polymer degradation and Stability 63 (1999) 273-278).*
Mats Galbe (Pretreatment of Lignocellulosic Materials for Efficient Bioethanol Production. Adv Biochem Engin/Biotechnol (2007)108: 41-65).*
Romero, et al (Journal of Chemistry and Chemical Engineering (2011), 5(10), 880-889.*
Gomes et al. Comparative Studies on Production of Cell Wall-Degrading Hydrolases by Trichoderma reesei and T. viride in Submerged and Solid-State Cultivations Isidore Gomes (Bangladesh J Microbiol, vol. 23, No. 2, Dec. 2006, pp. 149-155).*
Optimization of Solid State Fermentation Conditions for the Production of Cellulase by Using Trichoderma Reesei. European Journal of Applied Engineering and Scientific Research, 2012, 1 (4):196-200 Rajesha.*
Jan B. Kristensen (Use of Surface active additives in enzymatic hydrolysis of wheat straw lignocellulose, Enzyme and Microbial Technology 40 (2007) 888-895).*
Bradford, MM, "A Rapid and Sensitive Method for the Quantitation of Microgram Quantities of Protein Utilizing the Principle of Protein-Dye Binding," 1976 Analytical Biochem 72 pp. 248-254.
Davis, MW, "A Rapid Modified Method for Compositional Carbohydrate Analysis of Lignocellulosics by High pH Anion-Exchange Chromatography with Pulsed Amperometric Detection (HPAEC/PADP)," 1998 J of Wood Chem and Tech 18 pp. 235-252.
Liu, H, et al., "In Situ, Rapid, and Temporally Resolved Measurements of Cellulase Adsorption onto Lignocellulosic Substrates by UV-vis Spectrophotometry," 2010 Am Chem Soc 27 pp. 272-278.
Luo, X, et al., "Evaluation of Mountain Beetle-Infested Lodgepole Pine for Cellulosic Ethanol Production by Sulfate Pretreatment to Overcome Recalcitrance of Lignocellulose," 2010 Ind Eng Chem Res 49 pp. 8258-8266.
Wang, GS, et al., "Sulfite Pretreatment too Overcome Recalcitrance of Lignocellulose (SPORL) for Robust Enzymatic Saccharification of Hardwoods," 2009 Biotechno Prog 25 pp. 1086-1093.
Wood, TM, and Bhat, KM, "Methods for Measuring Cellulase Activities," 1988 Methods in Enzymology 160 pp. 87-112.
Zhu JY, et al., "Sulfite Pretreatment (SPORL) for Robust Enzymatic Saccharification of Spruce and Red Pine," 2009 Bioresource Tech 100 pp. 2411-2418.
Zhu JY, et al., "Specific Surface to Evaluate the Efficiencies of Milling and Pretreatment of Wood for Enzymatic Saccharification," 2009 Chem Eng Sci 64 pp. 474-485.
Zhu JY, et al., "On Energy Consumption for Size-Reduction and Yields from Subsequent Enzymatic Saccharification of Pretreated Lodgepole Pine," 2010 Bioresource Tech 101 pp. 2782-2792.
Zhu JY, et al., "High Titer Ethanol Production from Simultaneous Enzymatic Saccharification and Fermentation of Aspen at High Solids: A Comparison Between SPORL and Dilute Acid Pretreatments," 2011 Bioresource Tech 102 pp. 8921-8929.
Clark, T.A., et al., "Steam Explosion of the Softwood Pinus Radiata with Sulphur Dioxide Addition," 1989 Journal of Wood Chemistry and Technology 9 pp. 135-166.
Sewalt, V.J.H., et al., "Lignin Impact on Fiber Degradation. 3. Reversal of Inhibition of Enzymatic Hydrolysis by chemical Modification of Lignin and by Additives," 1997 J. Agric. Food Chem 45 pp. 1823-1828.

(Continued)

*Primary Examiner* — Kagnew H Gebreyesus
(74) *Attorney, Agent, or Firm* — John D. Fado; Lesley D. Shaw; Janet I. Stockhausen

(57) ABSTRACT

A system is provided for reducing non-specific binding of an enzyme to lignin to enhance an enzymatic processing of a lignocellulosic material. The enhancements provide economic and process advantages to any process that converts a lignocellulosic biomass into a product using an enzyme. Systems are provided comprising a reaction vessel; a lignocellulosic feedstock comprising a component selected from the group consisting of a hardwood, a softwood, or a non-wood material; an enzyme component including a cellulase, a hemicellulase, or a combination thereof; and, water. The reaction vessel can contain a combination of the lignocellulosic feedstock, the water, and the enzyme component at a pH ranging from about 5.2 to about 6.2; and, the lignocellulosic feedstock can be saccharified in the reaction vessel. Moreover, the systems can include a lignosulfonate, with or without a pH of about 5.2 to about 6.2, to also reduce non-specific binding and enhance enzymatic activity.

22 Claims, 22 Drawing Sheets

(56) References Cited

PUBLICATIONS

Liu, H., Zhu, J.Y. and Fu, S.Y., "Effects of Lignin-Metal Complexation on Enzymatic Hydrolysis of Cellulose," 2010 J. Agric. Food Chem 58 pp. 7233-7238.

Liu, Hao and Zhu, J.Y., "Eliminating inhibition of enzymatic hydrolysis by lignosulfonate in unwashed sulfite-pretreated aspen using metal salts," 2010 Bioresource Technology 101 pp. 9120-9127.

Berlin, Alex, et al., "Inhibition of cellulase, xylanase and B-glucosidase activities by softwood lignin preparations," 2006 Journal of Biotechnology 125 pp. 198-209.

Nakagame, Seiji, et al., "The Effect of Isolated Lignins, Obtained From a Range of Pretreated Lignocellulosic Substrates, on Enzymatic Hydrolysis," 2009 Biotechnology and Bioengineering 105 pp. 871-879.

Zhou, Haifeng, et al., "Lignosulfonate to Enhance Enzymatic Saccharification of Lignocelluloses: Role of Molecular Weight and Substrate Lignin," 2013 Industrial & Engineering Chemistry Research 52 pp. 8464-8470.

Lai, Chenhuan, et al., "Contrasting effects of hardwood and softwood organosolv lignins on enzymatic hydrolysis of lignocellulose," 2014 Bioresource Technology 163 pp. 320-327.

* cited by examiner

A

B

US 9,074,231 B2

REDUCING NON-SPECIFIC ENZYME BINDING TO ENHANCE LIGNOCELLULOSE CONVERSION

STATEMENT REGARDING FEDERALLY SPONSORED RESEARCH OR DEVELOPMENT

This invention is owned by the U.S. Federal Government. The U.S. Government has certain rights in the inventions disclosed herein.

BACKGROUND OF THE INVENTION

1. Field of the Invention

The teachings provided herein are generally directed to a system for reducing non-specific binding of an enzyme to lignin to enhance an enzymatic processing of a lignocellulosic material.

2. Description of the Related Art

Enzymatic conversion of a polysaccharide is a useful process for producing chemicals from sustainable resources, and polysaccharides are prevalent in lignocellulosic materials. An efficient utilization of the polysaccharides in a lignocellulosic biomass is desirable, for example, as lignocellulosic biomass is one of the most abundant natural resources on earth. As such, lignocelluloses can be used sustainably to produce biofuel and chemicals, used economically to provide a means of producing materials in developing countries or emerging economies, and used sensibly to mitigate climate change by reducing the reliance on fossil fuels. Currently, however, there is a need to improve the economic viability of these processes, as the state-of-the-art relies on an inefficient use of cellulase enzymes.

Lignocelluloses comprise lignin and polysaccharides: cellulose and hemicellulose. Whereas the polysaccharides can be hydrolyzed into sugars, the lignin is a phenolic polymer that can inhibit an enzymatic saccharification of the polysaccharides. It has been proposed that the inhibition can occur by at least the following problems: (i) a physical blockage problem that limits the ability of the cellulase to access the polysaccharides; and, (ii) a nonspecific adsorption problem, or binding, of the cellulase to lignin. The physical blockage problem can and has been addressed using certain chemical pretreatments that at least partially remove lignin that may block access of the cellulase to the cellulose, but the lignin content is often enriched relative to the polysaccharides due to the simultaneous removal of hemicelluloses during chemical pretreatment. As a result, the problem of nonspecific adsorption (or binding) of cellulase enzymes to lignin is not addressed and, moreover, can be exacerbated.

One of skill would appreciate a way of reducing the enzyme dosages required to achieve a desired level of saccharification, and reducing the nonspecific binding of the enzyme to lignin. Delignification processes are too expensive, complicated and, for at least these reasons, are not efficient ways of addressing the problems. Free lignin (separated from lignocelluloses) can be removed by further washing, but washing is an environmental concern as it uses too much water. Bound lignin (unseparated lignin on solids) can be blocked using surfactants or metals, but the levels required are too expensive.

Accordingly, the art would appreciate (i) a way of efficiently reducing the dosage of enzyme required to achieve a desired level of saccharification of a polysaccharide; (ii) a process that is environmentally friendly in that it does not require an abundance of water; and, (iii) a process that is economically efficient in that it doesn't require an expensive process step or a costly addition of chemicals to achieve the desired level of saccharification. It should be appreciated that the teachings provided herein are generally directed to a system for reducing non-specific binding of an enzyme to lignin to enhance an enzymatic processing of a lignocellulosic material and, as such, the benefits provided by the teachings herein may be utilized in any biorefinery process that uses an enzyme to convert a lignocellulosic material to a product.

SUMMARY

The teachings provided herein are generally directed to a system for reducing non-specific binding of an enzyme to lignin to enhance an enzymatic processing of a lignocellulosic material. The enhancements taught herein can provide economic and process advantages to any process that converts a lignocellulosic biomass into a product using an enzyme including, but not limited to, biofuel production.

The teachings are directed to a system comprising a reaction vessel; a lignocellulosic feedstock comprising a component selected from the group consisting of a hardwood, a softwood, or a non-wood material; an enzyme component including a cellulase, a hemicellulase, or a combination thereof; and, water. The reaction vessel can contain a combination of the lignocellulosic feedstock, the water, and the enzyme component at a pH ranging from about 5.2 to about 6.2; and, the lignocellulosic feedstock can be saccharified in the reaction vessel.

The teachings are also directed to a system for enhancing enzymatic saccharification of cellulose, the system containing a lignosulfonate additive. In these embodiments, the system can comprise a reaction vessel; a lignocellulosic feedstock comprising a component selected from the group consisting of a hardwood, a softwood, or a non-wood material, with the proviso that the feedstock does not contain a lignosulfonate; an enzyme component including a cellulase, a hemicellulase, or a combination thereof; a lignosulfonate additive having a component selected from the group consisting of a hardwood, a softwood, or a non-wood lignin; and, water. In these embodiments, the reaction vessel can contain a combination of the lignocellulosic feedstock, the water, the enzyme component, and the lignosulfonate additive; and, the lignocellulosic feedstock can be saccharified in the reaction vessel. In some embodiments, the reaction vessel can contain the combination of the lignocellulosic feedstock, the water, and the enzyme component at a pH ranging from about 5.2 to about 6.2.

In some embodiments, the systems can further comprise a pretreatment vessel for pretreating the lignocellulosic feedstock, the pretreatment vessel containing an aqueous solution of sulfite or bisulfite at a pH ranging from about 1.0 to about 5. In some embodiments, the systems can further comprise a fermentation vessel containing a yeast for fermenting the saccharified lignocellulosic feedstock. And, in some embodiments, the enzyme component can comprises *Trichoderma reesei*.

The teachings also include a method for enhancing enzymatic saccharification of cellulose. In these embodiments, the method can comprise obtaining a system discussed above and reacting the combination of the lignocellulosic feedstock, the water, and the enzyme component at the pH ranging from about 5.2 to about 6.2 to saccharify the lignocellulosic feedstock.

The teachings also include a method for enhancing enzymatic saccharification of cellulose. In these embodiments, the method can comprise obtaining a system discussed above and reacting the combination of the lignocellulosic feedstock, the water, the enzyme component, and the lignosulfonate additive at the pH ranging from about 5.2 to about 6.2 to saccharify the lignocellulosic feedstock.

In some embodiments, the reacting can occur at a pH ranging from about 5.5 to about 6.0. In some embodiments, the method further comprises pretreating the lignocellulosic feedstock in a pretreatment vessel containing an aqueous solution of sulfite or bisulfite at a pH ranging from about 1.0 to about 5. In some embodiments, the method further comprises fermenting the saccharified lignocellulosic feedstock in a fermentation vessel containing a yeast.

The teachings are also directed to a system for producing a biofuel. In these embodiments, the system can comprise a pretreatment vessel containing an aqueous solution of sulfite or bisulfite at a pH ranging from about 1.0 to about 5; a reaction vessel; a lignocellulosic feedstock comprising a component selected from the group consisting of a hardwood, a softwood, or a non-wood material; an enzyme component comprising *Trichoderma reesei*; a lignosulfonate comprising a component selected from the group consisting of a hardwood, a softwood, or a non-wood lignin; water; and, a fermentation vessel containing a yeast for fermenting the saccharified lignocellulosic feedstock. In these embodiments, the reaction vessel can contain the combination of the lignocellulosic feedstock, the water, the enzyme component, and the lignosulfonate at a pH ranging from about 5.2 to about 6.2. The lignocellulosic feedstock can be saccharified in the reaction vessel for fermentation; and, the saccharified lignocellulosic feedstock can be converted to ethanol in the fermentation vessel.

Accordingly, the teachings include methods of producing a biofuel. In these embodiments, the methods can include obtaining a system taught herein for producing a biofuel. The methods can include pretreating the lignocellulosic feedstock in the pretreatment vessel; reacting the combination of the lignocellulosic feedstock, the water, the enzyme component, and the lignosulfonate at the pH ranging from about 5.2 to about 6.2 to saccharify the lignocellulosic feedstock; and, fermenting the saccharified lignocellulosic feedstock to create a biofuel.

DETAILED DESCRIPTION OF THE INVENTION

Figure 1:
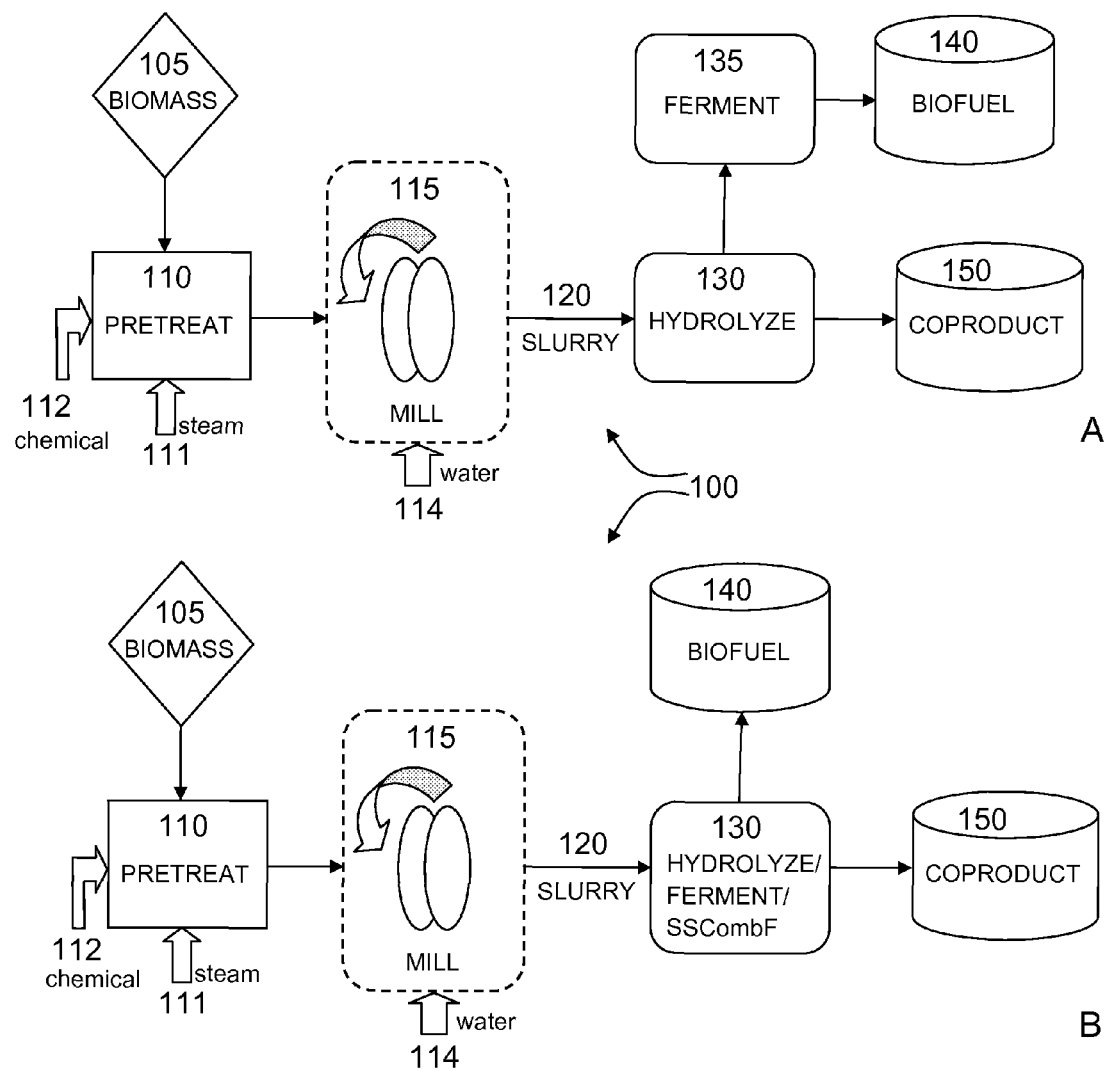
FIGS. 1A and 1B illustrate process flows for producing a biofuel, the process having separate or combined (SSCombF) hydrolysis and fermentation units, according to some embodiments.

The teachings provided herein are generally directed to a process for enhancing the enzymatic saccharification of a polysaccharide by reducing non-specific binding of a cellulase on a lignocellulosic substrate. The enhancements taught herein can provide economic and process advantages to process that include, but are not limited to, biofuel production.

The terms "lignocellulosic biomass," "lignocellulose," "biomass," "slurry," and "substrate," are examples of terms used herein that can be used interchangeably in most embodiments. The terms can be used to refer to a plant biomass that is composed of cellulose, hemicellulose, and lignin. The carbohydrate polymers (cellulose and hemicelluloses) are tightly bound to the lignin. Any lignocellulosic material can be used as the biomass among embodiments taught herein. Lignocellulosic biomass types can be grouped into four main categories, for example: (i) woody and non-woody materials, such as agricultural residues (including corn stover and sugarcane bagasse), (ii) crops dedicated for bioconversion, (iii) hardwood, softwood, wood residues (including sawmill and paper mill discards), and (iv) municipal paper and other industrial waste. In some embodiments. In some embodiments, the biomass can include food waste.

The terms "product", "co-product", "byproduct" and the like can be used interchangeably in many embodiments to refer to the product of an enzymatic hydrolysis of a lignocellulose, such as a hydrolysis product or fermentation product of the hydrolyzed product including, but not limited to, fuels, chemicals, materials, food, and feed. The terms "biofuel" and "fuel" can be used to refer to the fermentation product of a hydrolyzed lignocellulosic material. The terms "fermentation" or "ferment", for example, can be used to refer to the conversion of a sugar to an alcohol including, but not limited to, methanol, ethanol, propanol, butanol, etc. In some embodiments, the fermenting can include contacting sugars with an alcohol-producing biocatalyst, such as yeast or an alcohol-producing microbe. In some embodiments, the fermenting can include a simultaneous saccharification and combined-fermentation (SSCombF).

The terms "reaction conditions," "suitable conditions," "effective conditions," "fermentation conditions," "suitable amount," "suitable level," "effective amount," "effective level," and the like can be used in some embodiments to refer to conditions, amounts, or levels for the producing a biofuel and may include pH, temperature, atmosphere, additives, inoculants, oxygen-depleting agents, and the like. The term "pH-adjusting chemical" or "pH-adjusting agent" and the like can be used refer to a chemical or agent added to control pH in the processes taught herein. The pH-adjusting chemicals and agents can include pH-lowering agents, including mineral acids, organic acids, and acid salts; pH-raising agents, such as bases (e.g., ammonia, and ammonium salts); and buffering agents. Suitable pH-adjusting acids include, but are not limited to, hydrochloric acid, sulfuric acid, citric acid, formic acid, propioinic acid, acetic acid, butyric acid, phosphoric acid, and the like. Suitable pH-adjusting agents also include acid salts, such as sodium diacetate. Suitable bases include, but are not limited to, sodium hydroxide, calcium hydroxide, $Na_2CO_3$, and ammonium hydroxide. Buffering agents include, but are not limited to, $CaCO_3$, $NaHCO_3$, $NH_4Cl$, $NaH_2PO_4$, $K_2HPO_4$, and $KH_2PO_4$. The teachings also refer to the terms "amount", "concentration," "percent," and the like throughout, wherein unless stated otherwise, the terms refer to a weight basis, based on biomass weight.

The term "about" is used herein. The term can be used in some embodiments to include amounts or ranges close to amount or range recited or taught, as well as the exact amount or range recited or taught as though the term was not used as a modifier. As such, the phrase "about X", where X can be an amount or range, for example, includes the exact value of X. The term "substantially" is used herein. The teaching or recitation of "substantially" or "at least substantially," for example, can refer to a situation in which a desired value, such as a function or characteristic, is met. For example, a desired value may be to improve enzyme activity or reduce the non-specific binding of an enzyme or other protein. The non-specific binding of the protein may be obtained, for example, if it loses greater than about 10% of its non-specific binding, as long as the protein can perform it's intended use to a reasonable degree of efficacy, which may be an improvement in efficacy. In some embodiments, the reduction or gain in a value may be substantial in an amount greater than about 10%, about 12%, about 15%, about 20%, about 25%, about 35%, about 45%, about 50%, about 60%, about 70%, or any percentage therein in increments of 1%.

One of skill will appreciate that the systems and methods taught herein have a broad potential application and, as such, will potentially enhance the production of a variety of products from a variety of processes. The products can be used directly, indirectly after further conversion or, in fact, they may even be building-block chemicals for a variety of materials created in downstream processing including, for example, downstream chemical conversion, gasification, pyrolysis, and polymerization processes. One of skill will appreciate that a lignocellulose can be hydrolyzed and converted to ethanol, biodiesel, butanol, dimethylfuran, gamma-valerolactone, methanol, for example. As such, the products can be based on processes directed to utilizing single carbon molecules such as biogas and syngas, 5 and 6 carbon carbohydrates from starch, sucrose or cellulose; mixed 5 and 6 carbon carbohydrates stream derived from hemicelluloses, lignin, oils (plant-based or algal), organic solutions from grasses, and pyrolytic liquids.

Examples of processes can include C6 sugar processes yielding ethanol and animal feed from starch crops; Syngas processes yielding FT-diesel and naptha from lignocellulosic residues; and, C6/C5 sugar processes yielding ethanol, FT-diesel, and furfural from lignocellulosic crops. The processes can produce products that include, but are not limited to, succinic acid, itaconic acid, glutamic acid, adipic acid, 3-hydroxypropionic acid/aldehyde, isoprene/farnesene, aspartic acid; enzymes; organic acids, such as amino acids, namely lactic acid; vitamins and related compounds; antibiotics; and, xanthan. The processes can produce glucose derived chemicals that include, but are not limited to, sorbitol, levulinic acid, glucaric acid, hydroxymethylfurfural, 2,5-furan dicarboxylic acid, and p-xylene. The process can produce glycerol derived chemicals that can include, but are not limited to, propylene glycol, epichlorohydrin, 1,3-propanediol, 3-hydroxypropion aldehyde, acrylic acid, propylene, methanol (via syngas). The processes can produce other products that include, but are not limited to, biopolymers, such as polyethylene, polypropylene, polycarbonate, polyethylene terephthalate, polyvinyl chloride, polybutylene succinate, polylactic acid, polyhydroxyalkanoate, polyvinylchloride, polyamide, biodegradable starch, and regenerated cellulose. Such products can have a vast range of uses. For example, propylene glycol alone has a vast range of uses, including industrial applications such as unsaturated polyester resins, coolants and antifreeze, hydraulic and brake fluid, aircraft de-icing fluid, heat, transfer fluids, paints and coatings. There is also a market for high grade propylene glycol in fragrance, cosmetics and personal care, applications, food and flavourings, pet food/animal feed, and pharmaceutical formulations.

One of skill will appreciate that the systems and methods taught herein can be used food processing. Pectic enzymes are used in the food industry, for example. Pectinase includes a group of enzymes that break down a central part of plant cell walls, which is useful in food processing as the enzymes speed up the rate of reaction. In some embodiments, the processes can include the fruit juice and wine-making industries. In some embodiments, the processes can include the coffee- and tea-making industries, as well as the processing of waste coffee and tea into other chemicals.

Moreover, one of skill will appreciate that the systems and methods taught herein can be used the processing of textile fibers from plants. Enzymes including pectinase, for example, can be used with other cell wall degrading enzymes in the isolation of plant fibers, such as cotton, and reduce the need for toxic chemicals in such processes.

The systems taught herein can comprise a reaction vessel; a lignocellulosic feedstock comprising a component selected from the group consisting of a hardwood, a softwood, or a non-wood material; an enzyme component including a cellulase, a hemicellulase, or a combination thereof; and, water. The reaction vessel can contain a combination of the lignocellulosic feedstock, the water, and the enzyme component at a pH ranging from about 5.2 to about 6.2; and, the lignocellulosic feedstock can be saccharified in the reaction vessel.

The systems taught herein can also be designed for enhancing enzymatic saccharification of cellulose, the system containing a lignosulfonate additive. In these embodiments, the system can comprise a reaction vessel; a lignocellulosic feedstock comprising a component selected from the group consisting of a hardwood, a softwood, or a non-wood material, with the proviso that in some embodiments the feedstock does not contain a lignosulfonate; an enzyme component including a cellulase, a hemicellulase, or a combination thereof; a lignosulfonate additive having a component selected from the group consisting of a hardwood, a softwood, or a non-wood lignin; and, water. In these embodiments, the reaction vessel can contain a combination of the lignocellulosic feedstock, the water, the enzyme component, and the lignosulfonate additive; and, the lignocellulosic feedstock can be saccharified in the reaction vessel. In some embodiments, the reaction vessel can contain the combination of the lignocellulosic feedstock, the water, and the enzyme component at a pH ranging from about 5.2 to about 6.2. It should be appreciated that the lignocellulosic feedstock may contain lignosulfonate prior to addition of a lignosulfonate in some embodiments.

As such, one of skill will also appreciate that any of a number of enzymes can be used with the teachings herein. In fact, any lignocellulolytic enzyme may be used. In some embodiments, the enzyme or enzyme cocktail can comprise, for example, a cellulase or a hemicellulase. In some embodiments, the enzyme or enzyme cocktail can comprise a glucosidase, a xylanase, a lactase, an amylase, a chitinase, a sucrase, or a maltase. In some embodiments, the enzyme or enzyme cocktail can comprise a glycoside hydrolase (any one or any combination of enzymes from families 1-128), a polysaccharide lyase, a glycosyl transferase, or a carbohydrate esterase. In some embodiments the enzyme or enzyme cocktail can comprise, for example, glucosidase, β-glucosidase, cellobiohydrolase I, cellobiohydrolase II, endo-glucanase, exo-glucanase, endo-xylanase, exo-xylanase, xylosidase, arabinofuranosidase, alpha-glucuronidase, mannanase, galactinase, copper-dependent polysaccharide monooxygenases (GH61 and CBM33) and xyloglucanase. In some embodiments, the enzyme component can comprise *Trichoderma reesei*.

In some embodiments, the systems can further comprise a pretreatment vessel for pretreating the lignocellulosic feedstock, the pretreatment vessel containing an aqueous solution of sulfite or bisulfite, including $SO_2$, at a pH ranging from about 1.0 to about 5, 1.2 to about 5, 1.3 to about 5, 1.0 to about 4.0, from about 1.6 to about 4.9, from about 1.7 to about 4.8, from about 1.8 to about 4.7, from about 1.9 to about 4.6, from about 2.0 to about 4.5, from about 2.2 to about 4.2, from about 2.4 to about 4.0, from about 2.6 to about 3.8, from about 2.8 to about 3.6, from about 3.0 to about 3.4, or any pH or pH range therein in increments of 0.1. In some embodiments, the systems can further comprise a pretreatment vessel for pretreating the lignocellulosic feedstock, the pretreatment vessel containing a dilute acid, alkali, or any other non-sulfite-containing chemicals known to one of skill in the art. It should be appreciated that the term "dilute acid" can be used, in some embodiments, to refer to a concentration of an acid ranging from 0.1% to 10.0% concentration by weight of acid in solution. The range of acid can be, for example, from about 0.5% to about 4.5%, from about 5.0 to about 10%, about 1.0%, about 3.0%, about 5.0%, about 7.0%, about 10.0%, or any 0.1% increment therein. Example acids can include sulfuric acid, oxalic acid, and acetic acid in some embodiments. One of skill will appreciate that other acids may be suitable. It should be appreciated that the term "alkali" can be used, in some embodiments, to refer to a concentration of an alkali ranging from 1.0% to 15.0% concentration by weight of alkali in solution. The range of alkali can be, for example, from about 0.5% to about 4.5%, from about 5.0 to about 15%, about 1.0%, about 3.0%, about 5.0%, about 7.0%, about 10.0%, about 12%, about 14%, about 15%, or any 0.1% increment therein. Example alkali can include ammonia, NaOH, $CaOH_2$, $CaCO_3$ or a combination thereof, in some embodiments. One of skill will appreciate that other alkali sources may be suitable.

One of skill will be able to select a suitable reaction time and temperature for pretreatment of a lignocellulosic feedstock from a variety of possible pretreatment times and temperatures. Such selection can be based on the substrates, reagents, and environmental conditions of reaction. In some embodiments, the pretreatment temperature can range from about 100° C. to about 250° C., from about 110° C. to about 240° C., from about 120° C. to about 230° C., from about 130° C. to about 220° C., from about 140° C. to about 210° C., from about 145° C. to about 205° C., from about 150° C. to about 200° C., from about 140° C. to about 190° C., from about 145° C. to about 195° C., about 140° C., about 150° C., about 160° C., about 170° C., about 180° C., about 190° C., about 200° C., or any range of temperatures or temperature therein in increments of 1° C. Likewise, one of skill can select a suitable reaction time to match the selected reaction temperature. In some embodiments, the reaction time can range from about 1 minute to 2 hours, from about 2 minutes to 1.75 hours, from about 3 minutes to 1.5 hours, from about 5 minutes to 2 hours, from about 10 minutes to 2 hours, from about 15 minutes to 2 hours, from about 30 minutes to 1.5 hours, from about 20 minutes to 1.5 hours, from about 25 minutes to 1.25 hours, from about 30 minutes to 1.0 hour, from about 45 minutes to 1.5 hours, from about 45 minutes to 1.0 hour, from about 60 minutes to 1.25 hours, about 30 minutes, about 45 minutes, about 60 minutes, about 75 minutes, about 90 minutes, or any range therein or time therein in increments of 1 minute.

In some embodiments, the systems can further comprise a fermentation vessel containing a yeast for fermenting the saccharified lignocellulosic feedstock. In some embodiments, the yeast can include strains from a *Pichia* or *Saccharomyces* species. In some embodiments, the yeast can be *Saccharomyces cerevisiae*. In some embodiments, the fermenting is effected by bacteria. For example, the bacteria can be *Clostridium acetobutylicum* (e.g., when butanol is the desired fermentation product) or *Corynebacterium glutamicum* (e.g., when monosodium glutamate (MSG) is the desired fermentation product). In some embodiments, the micro-organism (e.g. yeast or bacteria) can be a genetically modified micro-organism. In some instances, the organism can be yeast or other organism having or modified to be active in the presence of high concentrations of alcohol.

One of skill will appreciate that the fermentation of, hydrolyzed product, glucose into ethanol can be carried out using any of a variety of agents, and any known agent can be used with the teachings herein. For example, *Saccharomyces cerevisiae* yeast or *Zymomonas mobilis* bacteria can be used in some embodiments. *Saccharomyces cerevisiae* and related species have the ability to utilize a wide range of hexoses such as glucose, fructose, sucrose, galactose, maltose and maltotriose to produce a high yield of ethanol. Standard fermenting conditions known to one of skill can be used in many embodiments taught herein. The yeasts that can be used include brewers' yeasts and include, but are not limited to, *Saccharomyces cerevisiae* and *Saccharomyces uvarum*. Non-conventional yeasts, can be used in some embodiments and include, but are not limited to *Kuyberomyces lactis, Yarrowia lipolytica, Hansenula polymorpha* and *Pichia pastoris*. Microorganisms other than yeast can be used and include, but are not limited to cellulolytic fungi, such as *Aspergillus niger, Trichoderma reesei, Trichoderma longibrachiatum* and *Trichoderma viride*. In some embodiments, the process can include the use of a bacteria including, but not limited to, *Clostridium thermocellum, Clostridium cellulovorans* or *Clostridium Ijungdahlii*.

The systems that are represented herein are numerous, as one of skill can enhance the utilization of enzymes in any such system that converts a lignocellulosic material. As such, the methods taught herein are meant to enhance any process that enzymatically converts a lignocellulose into a product that can be used directly or indirectly. For example, the systems can be designed for producing an alcohol, such as a biofuel. In these embodiments, the system can comprise a pretreatment vessel containing an aqueous solution of acid; alkali; or, sulfite or bisulfite at a pH ranging from about 1.0 to about 5; a reaction vessel; a lignocellulosic feedstock comprising a component selected from the group consisting of a hardwood, a softwood, or a non-wood material; an enzyme component comprising *Trichoderma reesei*; a lignosulfonate comprising a component selected from the group consisting of a hardwood, a softwood, or a non-wood lignin; water; and, a fermentation vessel containing a yeast for fermenting the saccharified lignocellulosic feedstock. In these embodiments, the reaction vessel can contain the combination of the lignocellulosic feedstock, the water, the enzyme component, and the lignosulfonate at a pH ranging from about 5.2 to about 6.2. The lignocellulosic feedstock can be saccharified in the reaction vessel for fermentation; and, the saccharified lignocellulosic feedstock can be converted to ethanol in the fermentation vessel.

FIGS. 1A and 1B illustrate process flows for producing a biofuel, the process having separate or combined (SSCombF) hydrolysis and fermentation units, according to some embodiments. The process 100 can include a lignocellulosic biomass 105 pretreated in a reactor 110 in aqueous or steam pretreatment mode with or without steam 111 explosion. The chemicals 112 used in pretreatment can be any suitable chemical or mixture known to one of skill, for example, sulfuric acid, or a base. A sulfite based pretreatments, such as a sulfite pretreatment to overcome recalcitrance of lignocellulose (SPORL) and/or and $SO_2$ catalyzed steam pretreatments may be desired in some embodiments. See, for examples, Zhu J Y et al., Bioresource Technology, 100(8): 2411-2418 (2009); and Wang G S, et al. Biotechnology Progress 25(4):1086-1093(2009), each of which is hereby incorporated herein by reference in its entirety.

Without separating the solid and liquid fractions of the pretreated lignocelluloses, further size reduction of the solids can be applied by feeding the pretreated material (both the solid and liquid fractions) into a disk mill, twin screw extruder 115 or any other mechanical device known to one of skill as suitable for this purpose, adding water 114 as needed. Size reduction is optional, especially for a non-woody biomass including, but not limited to, a herbaceous biomass or an agricultural residue. The pH of the whole slurry 120 can then be adjusted, e.g., between about 5.0 to about 8.0 in some embodiments. In some embodiments, the pH may range from about 4.0 to about 7.5, from about 4.5 to about 7.0, from about 5.5 to about 6.5, from about 5.0 to about 6.0, from about 5.2 to about 6.2, from about 5.3 to about 6.3, from about 5.3 to about 6.2, from about 5.4 to about 6.1, about 5.2, about 5.3, about 5.4, about 5.5, about 5.6, about 5.7, about 5.8, about 5.9, about 6.0, about 6.1, about 6.2, any range of pH or individual pH therein in increments of 0.1. The pH can be adjusted using any suitable base. In some embodiments, the pH can be adjusted using a base comprising NaOH, $Ca(OH)_2$, or a combination thereof. Buffer can be used to maintain the pH in the subsequent reactions. The whole slurry 120 can then be directly used for the SSCombF step 125 or a sequential enzymatic hydrolysis 130 and conversion 135 without a separate solid substrate washing step. The whole slurry 120 can be diluted to the desired solid consistency before the SSCombF 125 and enzymatic hydrolysis 130 steps in the process of producing the biofuel 140. A lignosulfate 150 and/or other co-product can also be produced from the process.

In some embodiments, a lignosulfate can be added, for example, to enhance the enzymatic hydrolysis. In some embodiments, the lignosulfonate can be included with a hydrolysate. And, in some embodiments, the lignosulfonate can be an off-the-shelf commercial product. When a sulfite based pretreatment is used, such as SPORL and/or $SO_2$ catalyzed steam pretreatments, the pretreatment hydrolysate comprises a lignosulfonate, and the process 100 can be directly used to include the lignosulfonate with little-to-no modification. When a pretreatment does not involve sulfite, the lignosulfonate can be added, for example, before the pH adjustment.

Figure 2:
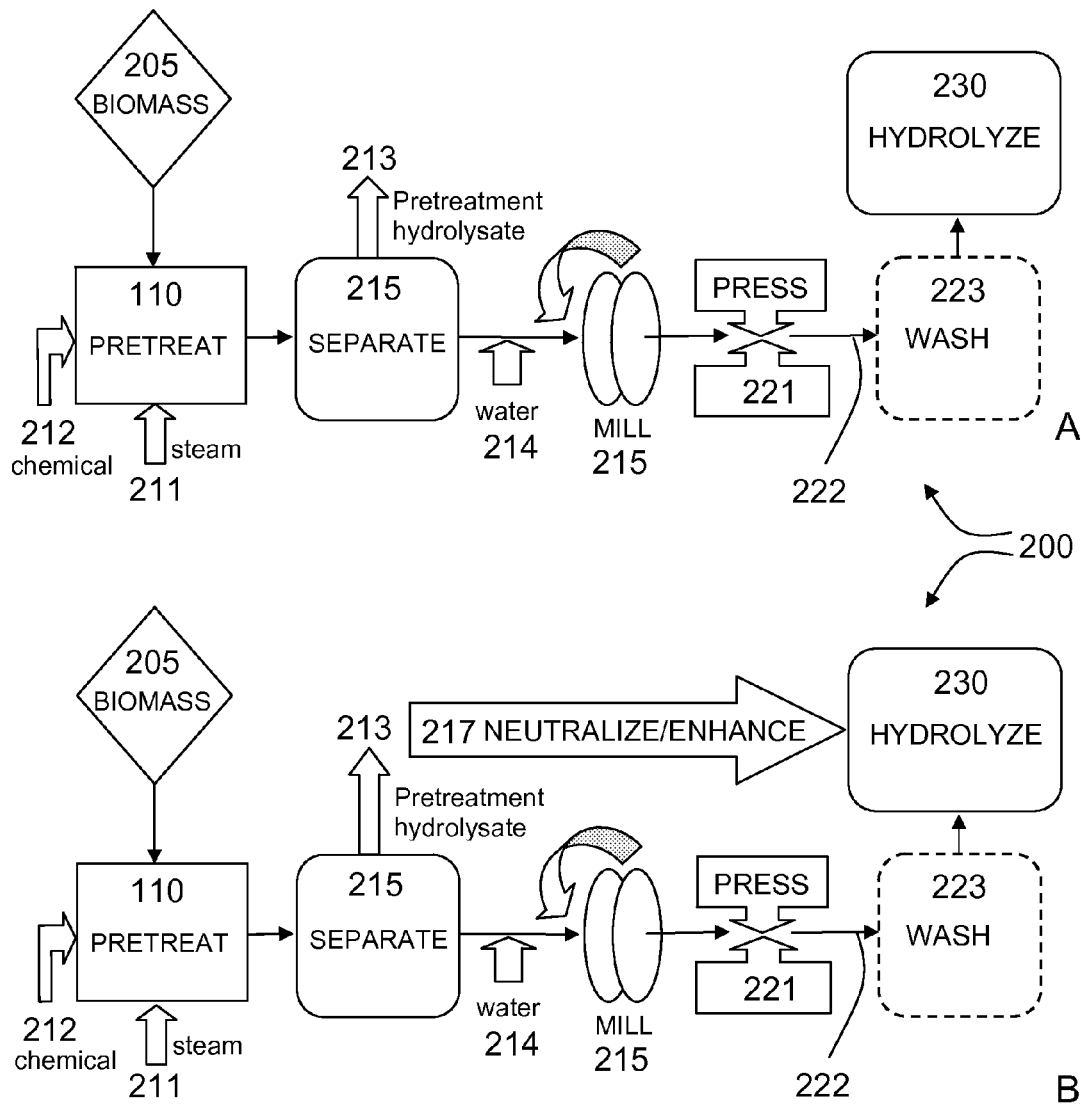
FIGS. 2A and 2B illustrate process flows for enzymatic hydrolysis of a lignocellulose, the process including the removal and re-use of a pretreatment hydrolysate as a lignosulfonate additive to enhance hydrolysis, according to some embodiments.

FIGS. 2A and 2B illustrate process flows for enzymatic hydrolysis of a lignocellulose, the process including the removal and re-use of a pretreatment hydrolysate as a lignosulfonate additive to enhance hydrolysis, according to some embodiments. The process 200 can include a lignocellulosic biomass 205 pretreated in a reactor 210 in aqueous or steam pretreatment mode with or without steam 211 explosion. The chemicals 212 used in pretreatment can be any suitable chemical or mixture known to one of skill, for example, sulfuric acid, or a base. A sulfite based pretreatments, such as a sulfite pretreatment to overcome recalcitrance of lignocellulose (SPORL) and/or and $SO_2$ catalyzed steam pretreatments may be desired in some embodiments. The pretreatment hydrolysate 213 can be removed, in some embodiments. In some embodiments the pretreatment hydrolysate can be pH-adjusted 217 for re-use to enhance enzymatic hydrolysis. Further size reduction of the solids can be applied by feeding the pretreated material (both the solid and liquid fractions) into a disk mill, twin screw extruder 215 or any other mechanical device known to one of skill as suitable for this purpose, adding water 214 as needed. The whole slurry (not shown) can then be dewated using a press 221 to create a solid substrate 222. The solid substrate 222 is optionally washed 223 for enzymatic hydrolysis 230. One of skill will appreciate that the "solid" substrate is merely a dewatered substrate having a consistency, for example, of greater than 20%, greater than 25%, greater than 30%, greater than 35%, or greater than 40%, or any range therein, in some embodiments.

One of skill will appreciate that the design of a system herein will include the selection of several parameters, such as reactants, reaction conditions, effective amounts, effective levels, and the like. Such parameters may include pH, temperature, atmosphere, additives, inoculants, oxygen-depleting agents, and the like. Any reaction conditions known to one of skill as suitable for a particular enzyme/substrate system can be used, in some embodiments.

In some embodiments, the pretreatment hydrolysate may not be used as an additive for the enzymatic hydrolysis. In some embodiments, the pretreatment hydrolysate is added to the prewashed solid to enhance the enzymatic hydrolysis. And, in some embodiments, a lignosulfonate can be added to the substrate before the enzymatic hydrolysis to either increase the amount of lignosulfonate, add a different type of lignosulfonate, or ensure that some lignosulfonate is present to enhance the enzymatic hydrolysis.

The methods of using the systems can be designed for reducing non-specific binding of an enzyme to lignin to enhance an enzymatic processing of a lignocellulosic material such as, for example, enhancing enzymatic saccharification of cellulose. In these embodiments, the method can comprise obtaining a system discussed above and reacting the combination of the lignocellulosic feedstock, the water, and the enzyme component at the pH ranging from about 5.2 to about 6.2 to saccharify the lignocellulosic feedstock.

The methods of using the systems can be designed for enhancing enzymatic saccharification of cellulose. In these embodiments, the method can comprise obtaining a system discussed above and reacting the combination of the lignocellulosic feedstock, the water, the enzyme component, and the lignosulfonate additive at the pH ranging from about 5.2 to about 6.2 to saccharify the lignocellulosic feedstock.

In some embodiments, the reaction can occur at a pH ranging from about 5.5 to about 6.0. In some embodiments, the method further comprises pretreating the lignocellulosic feedstock in a pretreatment vessel containing an aqueous solution of sulfite or bisulfite at a pH ranging from about 1.0 to about 5. In some embodiments, the method further comprises fermenting the saccharified lignocellulosic feedstock in a fermentation vessel containing a yeast.

The methods of using the systems can be designed for producing a biofuel. In these embodiments, the methods can include obtaining a system taught herein for producing a biofuel. The methods can include pretreating the lignocellulosic feedstock in the pretreatment vessel; reacting the combination of the lignocellulosic feedstock, the water, the enzyme component, and the lignosulfonate at the pH ranging from about 5.2 to about 6.2 to saccharify the lignocellulosic feedstock; and, fermenting the saccharified lignocellulosic feedstock to create a biofuel.

One of skill will appreciate that the systems and methods taught herein provide processes that promote an enzyme activity on lignocellulosic materials that is a substantial improvement over current state-of-the-art. In some embodiments, the improvement is substantial when it is about 5%, about 10%, about 15%, about 20%, about 25%, about 30%, about 35%, about 40%, about 45%, about 50%, about 55%, about 60%, about 65%, about 70%, about 80%, about 90%, about 95%, about 98%, about 100%, or any improvement therein in increments of 1%. For example, an improvement can be a substantial improvement over a state-of-the-art process that uses a hydrolyzes a lignocellulosic material at a pH of about 4.7 to about 5.0, or any pH or pH range therein in increments of 0.1. In some embodiments, a system or method has an activity that is a substantial improvement over a current state-of-the-art system or method using a pH at or about pH 4.7, at or about pH 4.8, at or about pH 4.9, at or about pH 5.0; wherein, the current state-of-the-art process does not use a pH at or about pH 5.2, at or about pH 5.3, at or about pH 5.4, at or about pH 5.5, at or about pH 5.6, at or about pH 5.7, at or about pH 5.8, at or about pH 5.9, at or about pH 6.0, at or about pH 6.1, at or about pH 6.2, at or about pH 6.3, at or about pH 6.4, or at or about pH 6.5. In some embodiments, a system or method has an activity that is a substantial improvement over a current state-of-the-art system or method using a pH at or about pH 4.7, at or about pH 4.8, at or about pH 4.9, at or about pH 5.0; wherein, the current state-of-the-art process does not use a lignosulfonate additive, or a hydrolysate containing lignosulfonate, optionally in combination with a pH at or about pH 5.2, at or about pH 5.3, at or about pH 5.4, at or about pH 5.5, at or about pH 5.6, at or about pH 5.7, at or about pH 5.8, at or about pH 5.9, at or about pH 6.0, at or about pH 6.1, at or about pH 6.2, at or about pH 6.3, at or about pH 6.4, or at or about pH 6.5.

One of skill will also be aware of the enzymatic saccharification reaction temperature and time variables that can be used in the reactions taught herein. In some embodiments, enzymatic reaction time can range from about 1 hour to about 200 hours, from about 1 hour to about 175 hours, from about 1 hour to about 150 hours, from about 1 hour to about 125 hours, from about 1 hour to about 100 hours, from about 1 hour to about 75 hours, from about 1 hour to about 50 hours, from about 1 hour to about 25 hours, from about 1 hour to about 20 hours, from about 1 hour to about 10 hours, from about 1 hour to about 5 hours, or any range therein. In some embodiments, enzymatic reaction time can range from about 5 hours to about 200 hours, from about 5 hours to about 175 hours, from about 5 hours to about 150 hours, from about 5 hours to about 125 hours, from about 5 hours to about 100 hours, from about 5 hours to about 75 hours, from about 5 hours to about 50 hours, from about 5 hours to about 25 hours, from about 5 hours to about 20 hours, from about 5 hours to about 10 hours. In some embodiments, the enzymatic reaction time can be about 5 hours, about 10 hours, about 15 hours, about 10 hours, about 25 hours, about 30 hours, about 35 hours, about 40 hours, about 45 hours, about 55 hours, about 65 hours, about 75 hours, about 85 hours, about 95 hours, about 105 hours, about 125 hours, about 150 hours, about 175 hours, 200 hours, or any time therein in increments of 1 hour.

Likewise, one of skill will appreciate that the enzymatic saccharification reaction temperature can be any reaction temperature known to one of skill for use with a particular enzyme/substrate reaction. In some embodiments, the temperature can range from about 20° C. to about 95° C., from about 25° C. to about 95° C., from about 30° C. to about 95° C., from about 35° C. to about 95° C., from about 40° C. to about 95° C., from about 45° C. to about 95° C., from about 50° C. to about 95° C., from about 55° C. to about 95° C., from about 60° C. to about 95° C., from about 65° C. to about 95° C., from about 70° C. to about 95° C., from about 20° C. to about 90° C., from about 20° C. to about 85° C., from about 20° C. to about 80° C., from about 20° C. to about 75° C., from about 20° C. to about 70° C., from about 20° C. to about 65° C., from about 20° C. to about 60° C., from about 20° C. to about 55° C., from about 20° C. to about 50° C., from about 20° C. to about 45° C., from about 20° C. to about 40° C., from about 20° C. to about 35° C., or any range therein in increments of 1° C. In some embodiments, the reaction temperature ranges from about 40° C. to about 65° C., from about 40° C. to about 60° C., from about 40° C. to about 55° C., from about 40° C. to about 50° C., or any range therein in increments of 1° C. In some embodiments, the enzymatic reaction temperature ranges from about 45° C. to about 55° C. In some embodiments, the reaction temperature is about 25° C., about 35° C., about 45° C., about 55° C., about 65° C., or any temperature therein in increments of 1° C.

EXAMPLES

The following examples illustrate, but do not limit, the scope of the teachings or claims. A person of skill in the art will recognize, or be able to ascertain using no more than routine experimentation, that there are many equivalents to the specific embodiments described herein.

Example 1

Materials and Methods

Materials

Commercial cellulase enzymes CELLUCLAST 1.5L, Novozyme 188 (β-glucosidase), and CELLIC CTec2 (abbreviated CTec2) were generously provided by Novozymes North America (Franklinton, N.C., USA). BIO-RAD (Bradford) protein assay kit and Bovine serum albumin (BSA) were purchased from Bio-Rad Laboratories (Hercules, Calif.). BSA was used as standard to calibrate the protein content of CTec2 by the Bradford method (See, M. Bradford. Analytical Biochemistry 72:248-254(1976), hereby incorporated herein by reference in it's entirety). The protein concentration of CTec2 was 73.6 mg/mL and its cellulase activity is 147 FPU/mL as calibrated by a known literature method (See T. M. Wood et al. Methods in Enzymology, Biomass, Part a, Cellulose and Hemicellulose. New York: Academic Press, Inc 160: 87-112(1988), hereby incorporated herein by reference in it's entirety). Sodium acetate buffer, sulfuric acid, and sodium bisulfite were obtained from Sigma-Aldrich (St. Louis, Mo.). High purity lignosulfonate D748 from softwood sulfite pulping was donated by LignoTech USA (Rothschild, Wis.). A pure cellulose sample is from commercial WHATMAN filter paper (Grade 3, Cat No 1003 150, Whatman International, England). The manufacturer specified ash content is 0.06%. A bleached Kraft pulp of loblolly pine (BKF-LbP) was obtained from a commercial source. The chemical composition was analyzed.

A lodgepole (*Pinus contorta*) tree killed by mountain pine beetle (*Dendroctonus ponderosae*) (estimated infestation age of 4 years, abbreviated BD4) and a live lodgepole pine tree (abbreviated FL) were harvested from the Canyon Lakes and the Sulphur Ranger District, Arapaho-Roosevelt National Forest, Colorado, respectively. Wood logs were debarked onsite, shipped to the U.S. Forest Service, Forest Products Laboratory, Madison, Wis., USA, and chipped using a laboratory chipper. The wood chips were then screened to remove all particles greater than 38 mm and less than 6 mm in length. The thickness of the accepted chips ranged from 1 to 5 mm. The chips were kept frozen at approximately −16° C. until used.

Substrate Production

Several substrates used in the following examples were produced from both the lodgepole pine and aspen wood chips using cooking or pretreatment method with different process chemistry. Table 1 lists the various substrates produced along with production process conditions. A laboratory wood pulping digester of capacity of 23 L was used for pretreatment and cooking (See J. Y. Zhu et al. Bioresource Technology 100: 2411-2418(2009)). The digester was heated by a steam jacket and rotated at 2 rpm for mixing. The oven dry (od) weight of wood chips in each pretreatment was 2 kg. The pretreatment liquid to wood ratio (L/W) was kept at 3 (v/w). The chemical charges, reaction temperature, and duration of different pretreatments or cooking are listed in Table 1.

In some examples, the pretreated wood chips were separated from the pretreatment hydrolysate. The pretreated wood chips were disk milled using plates of pattern D2B-505 with a disk plate gap of 1.0 mm and adjusted to a refiner inlet consistency of 10% with dilution water. The energy consumption for disk milling was recorded as described in Zhu J Y et al. Chem. Eng. Sci. 64(3):474-485(2009) and Zhu W et al. Bioresource Technology 101(8):2782-2792(2010), each of which is incorporated herein by reference in it's entirety. The size-reduced solids were directly dewatered to a solids content of approximately 30% by vacuum pressing in a canvas bag (as prewashing). To reduce the effects of remaining residue dissolved solids, acids, and ions, three lodgepole pine substrates were separately and thoroughly washed using 20 folds of water at 50° C., as indicated in Table 1, in addition to the prewash. The yields of solid substrate after washing were then determined from the weight and moisture content of the collected substrate. The chemical compositions of both the solid substrates along with the pretreatment hydrolysates were analyzed and described in Tables 2 and 3.

TABLE 1

| Sample Label[1] | Method | Chemical charges on wood (%) | T (° C.) | Duration @ T (min) | Separate washing |
|---|---|---|---|---|---|
| Lodgepole Pine - Solid lignocellulosic substrates | | | | | |
| SP-BD4-I | SPORL | $H_2SO_4$: 2.2 | 180 | 20 | YES |
| SP-BD4-II | | $NaHSO_3$: 8.0 | | | NO |
| SPH-FL | SPORL | $H_2SO_4$: 0 | 180 | 20 | YES |
| | | $NaHSO_3$: 6.0 | | | |
| KP-FL | Kraft Pulping | NaOH: 14.5 | 170 | 25 | YES |
| | | $Na_2S$: 10.6 | | | |
| Lodgepole Pine - Liquid substrates: Pretreatment hydrolysates or spent liquors | | | | | |
| L-BD4-II | SPORL | $H_2SO_4$: 2.2 | 180 | 20 | NA |
| L-BD4-T85-1 | | $NaHSO_3$: 8.0 | 185 | 5 | |
| L-BD4-T85-3 | | | 185 | 25 | |
| L-BD4-T85-5 | | | 185 | 45 | |
| Aspen | | | | | |
| SP-AS | SPORL | $H_2SO_4$: 1.1 | 170 | 25 | NO |
| | | $NaHSO_3$: 3.0 | | | |

TABLE 1-continued

| Sample Label[1] | Method | Chemical charges on wood (%) | T (° C.) | Duration @ T (min) | Separate washing |
|---|---|---|---|---|---|
| SPH-AS | | $H_2SO_4$: 0<br>$NaHSO_3$: 3.0 | 170 | 25 | |
| DA-AS | Dilute acid (DA) | $H_2SO_4$: 1.1 | 170 | 25 | |

[1]SP stands for SPORL; SPH stands for SPORL with sodium bisulfite only; KP stands for Kraft pulping; DA stands for dilute acid. SP-BD4-I and SP-BD4-II were produced under the exactly same conditions but at different time. AS stands for aspen.

TABLE 2

| Sample label | K lignin (%) | Glucan (%) | Xylan (%) | Mannan (%) | Solids yield (wt %) |
|---|---|---|---|---|---|
| *Untreated wood* | | | | | |
| BD4 | 28.6 | 41.9 | 5.5 | 11.7 | 100 |
| FL | 29.2 | 39.1 | 6.0 | 10.0 | 100 |

TABLE 2-continued

| Sample label | K lignin (%) | Glucan (%) | Xylan (%) | Mannan (%) | Solids yield (wt %) |
|---|---|---|---|---|---|
| Aspen | 20.2 | 45.6 | 16.4 | 1.4 | 100 |
| *Pretreated wood* | | | | | |
| SP-BD4-I | 37.9 | 54.3 | 1.0 | 0.9 | ND[1] |
| SP-BD4-II | 34.7 | 57.4 | 1.5 | 0.6 | 58.6 |
| SPH-FL | 34.2 | 49.4 | 3.4 | 4.6 | ND[1] |
| KF-FL | 16.6 | 59.1 | 7.6 | 5.4 | 48.4 |
| SP-AS | 28.1 | 66.2 | 1.9 | 0.3 | 58.2 |
| SPH-AS | 22.2 | 66.6 | 5.3 | 0.8 | 60.9 |
| DA-AS | 30.0 | 61.6 | 3.3 | 0.4 | 63.5 |
| BKF-LbP | 0.1 | 80.1 | 5.8 | 9.3 | |

[1]Not determined

TABLE 3

| Liquid substrate | Glucose (g/L) | Lignosulfonate (g/L) |
|---|---|---|
| L-BD4-II | 12.20 | 87.2 |
| L-BD4-T85-1 | 2.95 | 53.1 |
| L-BD4-T85-3 | 5.34 | 124.0 |
| L-BD4-T85-5 | 7.18 | 141.1 |

The pretreatment hydrolysate was pH adjusted using NaOH to the desired pH before applied to the suspension of solid lignocellulosic substrate for enzymatic hydrolysis. The glucose was measured using a glucose analyzer. The amount of lignosulfonate in the pretreatment spent liquor hydrolysate was estimated based on the difference between the amount of Klason lignin measured in the untreated wood and pretreated solid substrate, and therefore was expressed as Klason lignin.

Another set of dilute acid (DA) and SPORL pretreatments were employed to produce four lignocellulosic solid substrates from the beetle-killed lodgepole pine wood chips (BD4) using a 23 L rotating pulping digester. (See Id and J. Y. Zhu et al. Bioresource Technology 100:2411-2418(2009); and, J. Y. Zhu et al. Bioresource Technology 102:8921-8929 (2011), each of which is hereby incorporated herein by reference in it's entirety). The pretreatment conditions such as temperature and duration, sulfuric acid and sodium bisulfite dosages, and liquid to solid ratio (L/W) for DA and SPORL are listed in Table 4.

TABLE 4

| Pretreated substrate label[1] | Pretreatment | Chemical dosages on wood (wt %) | T (° C.) | Duration @ T (min) | Separate washing |
|---|---|---|---|---|---|
| DA | Dilute acid (DA) | $H_2SO_4$: 2.5 | 175 | 25 | YES |
| SP-B2 | SPORL | $H_2SO_4$: 2.5<br>$NaHSO_3$: 2.0 | 175 | 25 | YES |
| SP-B4 | SPORL | $H_2SO_4$: 2.5<br>$NaHSO_3$: 4.0 | 175 | 25 | YES |
| SP-B6 | SPORL | $H_2SO_4$: 2.5<br>$NaHSO_3$: 6.0 | 175 | 25 | YES |

[1]DA stands for dilute acid. SP stands for SPORL. B# stands for percent of sodium bisulfite loading on oven dry wood in SPORL pretreatment.

Again, the pretreated wood chips remained intact and were disk milled. The pretreated wood chips were first separated from the pretreatment spent liquor hydrolysate by a screen. A laboratory disk refiner (Andritz Sprout-Bauer Atmospheric Refiner, Springfield, Ohio) with a disk plate pattern of D2B-505 and a disk plate gap of 1.00 mm were used. The size-reduced solids were directly dewatered to a solids content of approximately 30% by vacuum pressing in a canvas bag (as prewashing). The chemical compositions of both the solid substrates along with the untreated wood chips, and hydrolysis lignin residues were analyzed. The results are listed in Table 5.

TABLE 5

| Sample label | K lignin (%) | Glucan (%) | Xylan (%) | Mannan (%) | Sum (%) | Sulfonic acid group content (mg/g lignin) |
|---|---|---|---|---|---|---|
| *Untreated lodgepole pine* | | | | | | |
| BD4 | 28.6 | 41.9 | 5.5 | 11.7 | 87.7 | |
| *Pretreated lodgepole pine* | | | | | | |
| DA | 58.0 | 38.4 | ND | ND | 96.1 | 0 |
| SP-B2 | 47.9 | 50.1 | 0.5 | ND | 98.3 | 4.23 |
| SP-B4 | 43.7 | 54.0 | 0.7 | ND | 98.3 | 6.37 |
| SP-B6 | 39.5 | 56.1 | 0.9 | ND | 96.3 | 11.53 |
| *Hydrolysis lignin residue* | | | | | | |
| L-DA | 85.8 | 8.2 | 0.4 | 1.0 | 95.4 | 0 |
| L-SP-B2 | 91.0 | 3.8 | 0.3 | 0.9 | 95.9 | 5.46 |
| L-SP-B4 | 91.4 | 3.6 | 0.3 | 1.0 | 96.3 | 8.07 |
| L-SP-B6 | 89.3 | 4.6 | 0.4 | 1.0 | 95.3 | 11.84 |

Enzymatic Hydrolysis

Enzymatic hydrolysis was conducted using commercial enzymes at 2% substrate solids (w/v) in 50-mL of buffer solutions on a shaker/incubator (Thermo Fisher Scientific, Model 4450, Waltham, Mass.) at 50° C. and 200 rpm. Acetate buffer solutions with different pH were used. Different ratios of sodium acetate and acetic acid varied pH values of the buffer solutions, for example, between 4.0 and 7.0. Enzymatic hydrolysis experiments were conducted using either a mixture of CELLUCLAST 1.5L supplemented with Novozyme 188 (β-glucosidase) or CTec2 alone. The loadings of CELLUCLAST 1.5L or CTec2 varied between 7.5 to 15 FPU/g glucan. The ratio of Novozyme 188 loading (in CBU) to CELLUCLAST 1.5L loading (in FPU) was 1.5. Selected hydrolysis experiments were carried out in duplicates to ensure experimental repeatability, and the hydrolysate was sampled periodically for glucose concentration analysis. Each data point was generally the average of two replicates, and the average relative standard deviation was approximately 2.5%.

Enzymatic hydrolysis of a pretreated solid substrate was conducted, for example, using CELLUCLAST 1.5L supplemented with Novozyme 188 (β-glucosidase) or CTec2 alone at 2% solids (w/v) in a flask on a shaker/incubator (Thermo Fisher Scientific, Model 4450, Waltham, Mass.) at 50° C. and 200 rpm. 1 g oven dry (od) weight of solid substrates was added into a 50 mL acetate buffer solution (50 mM) along with cellulase. The pH of the buffer solution was varied between 4.5 to 6.0 using different ratios of sodium acetate and acetic acid. The amount of glucose in the enzymatic hydrolysate was determined. Substrate enzymatic digestibility (SED), defined as the percent of substrate glucan enzymatically saccharified to glucose, was used to represent the enzymatic saccharification efficiency.

Hydrolysis Lignin Residue Preparation

Enzymatic hydrolysis lignin residues, L-DA, L-SP-B2, L-SP-B4, L-SP-B6 were prepared from the second set of four pretreated lodgepole pine substrates (Table 4), DA, SP-B2, SP-B4, SP-B6, respectively. Two-step enzymatic hydrolysis of each pretreated lodgepole pine substrate was conducted with overdose of CTec2 at a loading 20 FPU/g substrate in each step. The preparation procedure was the following: (1) milling the pretreated and disk-milled substrates in the same disk refiner using the same disk plates and disk plate gap described above; (2) enzymatically hydrolyzing approximately 16 g of the resultant substrate using CTec2 (20 FPU/g substrate) with solids loading of 2% (w/v) at pH 5.5 and 50° C. on a shaker at 200 rpm for 48 h; (3) decanting the supernatant after standing over night; (4) enzymatically hydrolyzing the remaining solids again by adding fresh CTec2 at the same loading under the same conditions described in step (2); (5) decanting the supernatant after centrifuge at 10000 rpm for 30 min; (6) washing the decanted lignin solid residue using distilled water at room temperature; (7) removing the residual protein on lignin residue from CTec2 used for enzymatic saccharification using an excess amount (~0.18 mg/g lignin residue) of Pronase K (6556, 30 units/mg protein) in a borax-$CaCl_2$ buffer of pH 8 at 5% (w/v) and 37° C. for 48 h; (8) decanting the supernatant after centrifuge at 10000 rpm for 30 min, then washing the resultant lignin residue using distilled water, 1.0 M NaCl, and distilled water sequentially; (9) deactivating the protease on lignin residues in deionized (DI) water at 100° C. for 2 h, washing twice using DI water; (10) drying the lignin residue at 50° C. for 60 h until no weight loss; (11) milling (WILEY mill) the lignin residues (Model #2, Arthur Thomas Co, Philadelphia, Pa.) using a 50 mesh screen. The sample was used for analysis and adsorption experiments.

Analytical Methods

The chemical compositions of the original and pretreated biomass were analyzed by the Analytical and Microscopy Laboratory of the Forest Products Laboratory as described previously. (See X. Luo et al. Ind. Eng. Chem. Res. 49:8258-8266(2010) hereby incorporated herein by reference in it's entirety). A two stage acid hydrolysis procedure was employed to hydrolyze WILEY-milled (model #2, Arthur Thomas Co, Philadelphia, Pa.) lignocellulosic substrates. The milled sample of 20 mesh (~1 mm) in size was hydrolyzed in two stages using sulfuric acid of 72% (v/v) at 30° C. for 1 h and 3.6% (v/v) at 120° C. for 1 h. The supernatant, after filtration using filter paper, was used for carbohydrate analysis using high-performance anion exchange chromatography with pulsed amperometric detection (HPAEC-PAD). (See M. W. Davis et al. Journal of Wood Chemistry and Technology 18:235-352(1998) hereby incorporated herein by reference in it's entirety.) Klason lignin (acid insoluble) retained on the filter paper was quantified gravimetrically after drying.

The saccharides in the pretreatment hydrolysates (spent liquors) were analyzed using a DIONEX HPLC system (ICS-3000) equipped with integrated amperometric detector and CARBOPAC PA1 guard and analytical columns at 20° C. Eluent was provided at a rate of 0.7 mL/min, according to the following gradient: 0→25 min, 100% water; 25.1→35 min, 30% water and 70% 0.1 M NaOH; 35.1→40 min, 100% water. To provide a stable baseline and detector sensitivity, 0.5 M NaOH at a rate of 0.3 mL/min was used as post-column eluent. To determine the oligomeric saccharides, the pretreatment hydrolysates were further hydrolyzed by adding an equal volume amount of sulfuric acid of 6% (v/v) to make sample with sulfuric acid concentration of about 3% (v/v). The acid hydrolysis was conducted in an autoclave at 120° C. for 60 min. All hydrolysate data reported were averages of triplicate measurements. For fast analysis, glucose in the enzymatic hydrolysate was measured in duplicate using a commercial glucose analyzer (YSI 2700S, YSI Inc., Yellow Springs, Ohio).

Cellulase Adsorption by Hydrolysis Residue Lignin

Cellulase adsorption experiments were conducted in acetic buffer solutions of pH 4.5, 4.8, 5.5, and 6.0 at 50° C. with hydrolysis lignin residues having a consistency of 2% (w/v) (using 0.100 g lignin and 4.900 g CTec2 solution). The initial concentrations of CTec2 were 25, 50, 100, 200, 400, 800 and 1600 mg protein/L. After incubation for 30 mins, the solution (50 mL) was centrifuged at 12000 rpm for 10 mins. The supernatant was again centrifuged at 12000 rpm for 10 mins. An aliquot of the final supernatant was placed into a sampling cuvette. The amount of cellulase adsorption by hydrolysis lignin residue was quantified using a UV-Vis spectrometer (Model 8453, Agilent Technologies, Palo Alto, Calif.) using a dual wavelength method. (See H. Liu et al. Langmuir 27:272-278(2011) hereby incorporated herein by reference in it's entirety.) The dual wavelength (276 nm and 400 nm) method can correct for spectral interferences from light scattering of small particles such as remaining insoluble lignin. The lignin solution without enzyme application was used as blank to correct for spectral absorption from dissolved lignin present in the lignin-cellulase solution. The amount of CTec2 adsorbed or bound on the hydrolysis lignin residue was calculated by subtracting the amount of free CTec2 in the supernatant from the total amount of CTec2 initially applied.

Determination of Adsorption Parameters

The Langmuir model was used to fit the adsorption isotherm data. The maximum cellulase adsorption capacity, σ, and cellulase adsorption equilibrium constant, $K_d$, were determined accordingly:

$$[CE] = \frac{\sigma[S_t][E_f]}{K_d + [E_f]}$$

where [CE] is the amount of adsorbed CTec2 in mg protein/L, [$E_f$] is free enzyme (e.g., CTec2) concentration in mg protein/mL, σ is the maximum adsorption capacity in mg protein/g lignin, [$S_t$] is the substrate concentration, i.e., 2 g/L for this study, and $K_d$ is the adsorption equilibrium constant in mg protein/mL. Affinity constant (A=1/$K_d$) and binding strength, S=Aσ can then be calculated.

Sulfur Content Analysis

The sulfur contents of the pretreated substrates were analyzed using ICP-MS (Ultima model, Horiba Jobin-Yvon, Edison, N.J., USA). Samples were weighed and then transferred to TEFLON digestion flasks. All samples were digested at 145° C. for 15 min in a microwave (MDS-2000, CEM Corp., Matthews, N.C., USA) using approximately 5 mL of $HNO_3$ and 3 mL of 30% $H_2O_2$ before ICP analysis.

Zeta Potential Measurement

Zeta potentials of hydrolysis lignin residues under different pH were measured in 50 mL buffer solutions on a shaker/incubator at 50° C. and 200 rpm. Buffer solutions of acetate with pH 4.5, 4.8, 5.5, 6.0 were used. The hydrolysis lignin residue concentration in the buffer solutions was 0.033% (w/w). The lignin solution was mixed using a magnetic stir for 30 min and stood for 60 min. The supernatant was tested by a Zeta Potential Analyzer (Zeta Plus, Brookhaven, USA). All zeta potential measurements were carried out in duplicates with seven readings in each experiment to ensure experimental repeatability. The averages are reported and the standard deviations were used as error bars in plotting.

Example 2

Saccharification is Enhanced in Lignocellulosic Substrates of Lodgepole Pine at an Elevated pH Enzymatic hydrolysis of each of three lodgepole pine substrates was conducted in buffer solutions of increasing pH.

Figure 3:
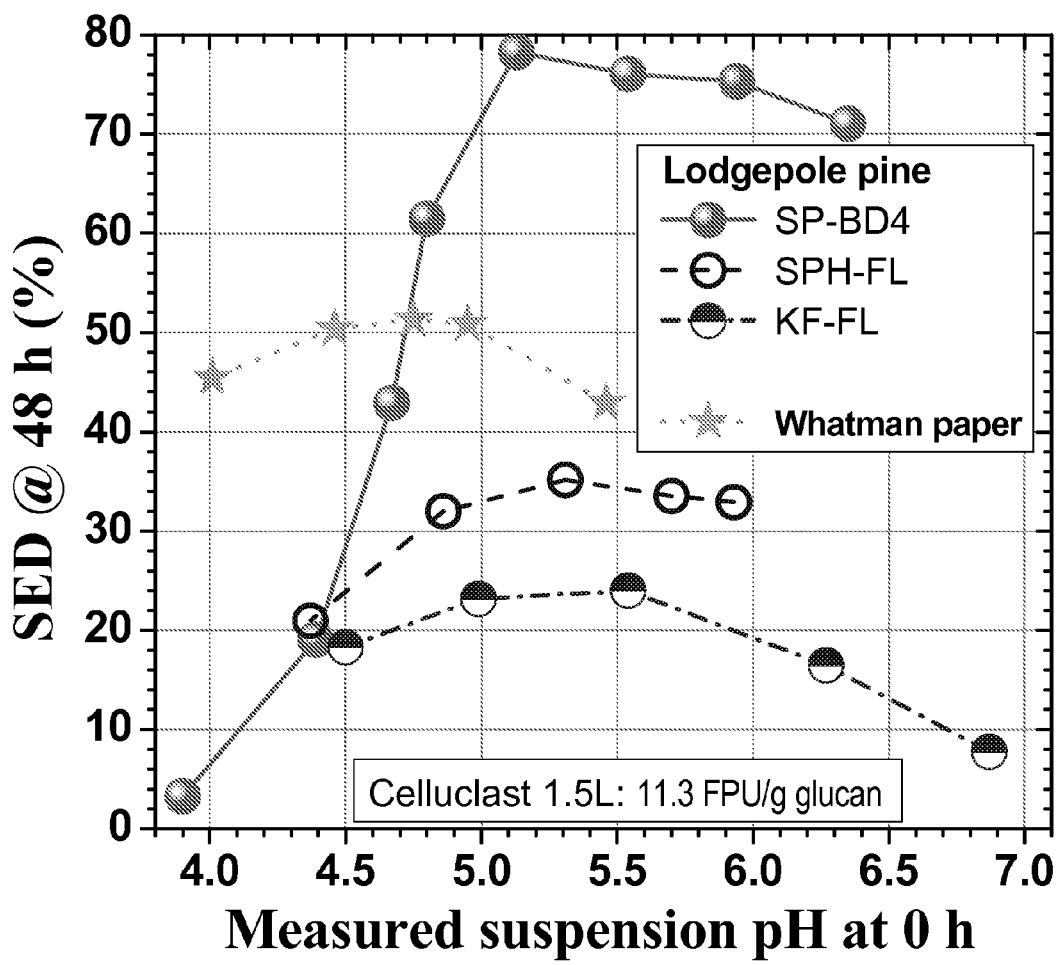
FIG. 3 illustrates the substrate enzyme digestibility (SED) of three lignocellulosic substrates of lodgepole pine in a pH range of about 4.5 to about 6.0, the substrates produced using SPORL pretreatment and kraft pulping, and mixture of CELLUCLAST 1.5L supplemented with Novozyme 188 according to some embodiments.

FIG. 3 illustrates the substrate enzyme digestibility (SED) of three lignocellulosic substrates of lodgepole pine in a pH range of about 4.5 to about 6.0. Two of the substrates were produced using SPORL pretreatment (SP-BD4-I, SPH-FL) and one of the substrates was produced using kraft pulping (KP-FL) according to some embodiments. The results clearly show that maximal substrate enzymatic digestibility (SED) at 48 h was achieved at measured pH of the suspension approximately 5.2 or higher for the three substrates, which contradicts the recommended use of pH 4.8 for the best results using CELLUCLAST 1.5 L per the enzyme provider, Novozyme. In fact, the optimal pH for the two lodgepole pine substrates produced by kraft pulping (KP-FL) and SPORL pretreatment using only bisulfite without acid (SPH-FL) was 5.5. For example, the SED of SP-BD4-I, produced by SPORL with sodium bisulfite and sulfuric acid (initial pretreatment liquor pH of approximately 2.0), increased rapidly when the pH was increased to 5.2, the SED at 48 h increasing from 43% to 80% at pH 5.2 (buffer pH 5.5). Using a commonly suggested hydrolysis pH of 4.8, in fact, is shown to cause significant reduction in cellulose saccharification.

Example 3

Saccharification is Enhanced in Lignocellulosic Substrates of Aspen at an Elevated pH Enzymatic hydrolysis of each of three aspen pine substrates was conducted in buffer solutions of increasing pH. The three aspen substrates were produced from dilute acid (DA) and SPORL with and without sulfuric acid.

Figure 4:
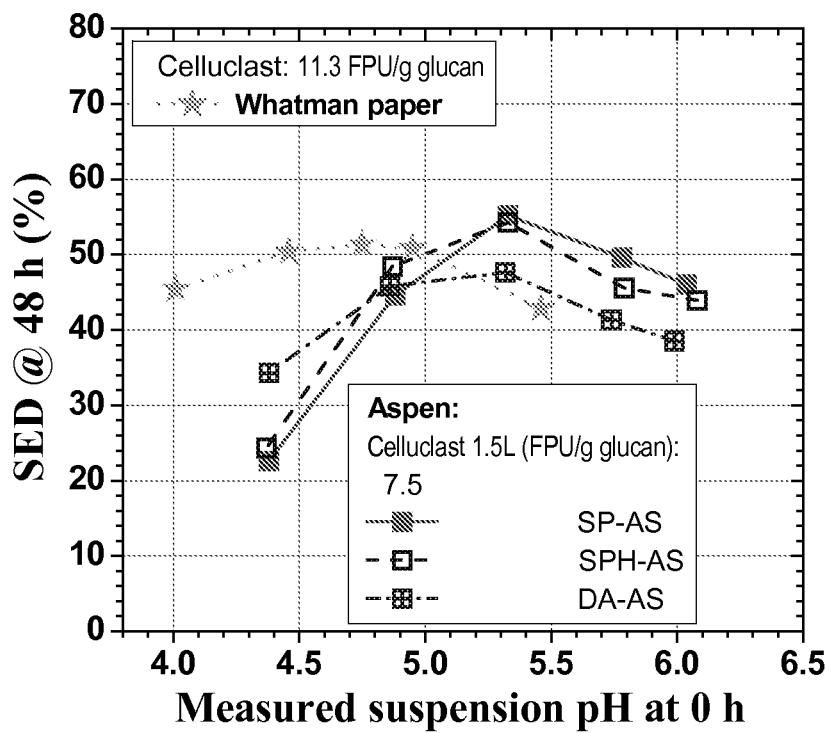
FIGS. 4A and 4B illustrate the substrate enzyme digestibility (SED) of three lignocellulosic substrates of aspen in a pH range of about 4.0 to about 7.0, the substrates produced using dilute acid (DA) and SPORL with and without sulfuric acid, and a mixture of CELLUCLAST 1.5L supplemented with Novozyme 188, according to some embodiments.
Figure 4:
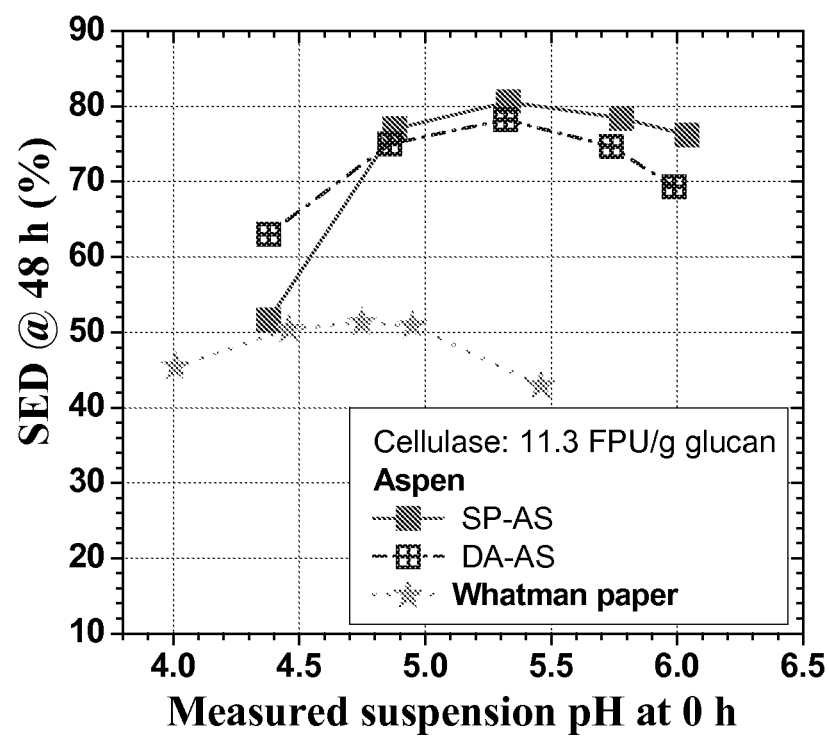

FIGS. 4A and 4B illustrate the substrate enzyme digestibility (SED) of three lignocellulosic substrates of aspen in a pH range of about 4.0 to about 7.0, the substrates produced using dilute acid (DA) and SPORL with and without sulfuric acid, according to some embodiments. The maximal SED at 48 h was achieved approximately at pH 5.3. The results show differences in pH response curves between lignocellulosic materials and pure cellulose, comparing the aspen substrates to WHATMAN paper. The optimal pH shifted from 4.8 for the pure cellulose to 5.3 for the lignocelluloses. As shown in FIG. 4A, the CELLUCLAST 1.5L loading of 7.5 FPU/g glucan increased SED from approximately 44%, 48%, and 46% . . . to 55%, 54%, and 48% for the SP-AS, SPH-AS, and DA-AS, respectively. One of skill will also appreciate that the elevated pH range used in the present examples is also favorable from a process standpoint, as the yeast fermentation step following the hydrolysis step in the production of biofuels, for example, can also work well at an elevated pH of around 5.5.

Example 4

The Data Suggests that the Cellulase Costs of a Near-Complete Conversion of a Lodgepole Pine can be Reduced by About 40% Using a SPORL Pretreatment and an Increased pH for the Enzymatic Hydrolysis The examples provided above show the effect of an increased pH. This example monitors the effect at near-complete cellulose conversion.

Figure 5:
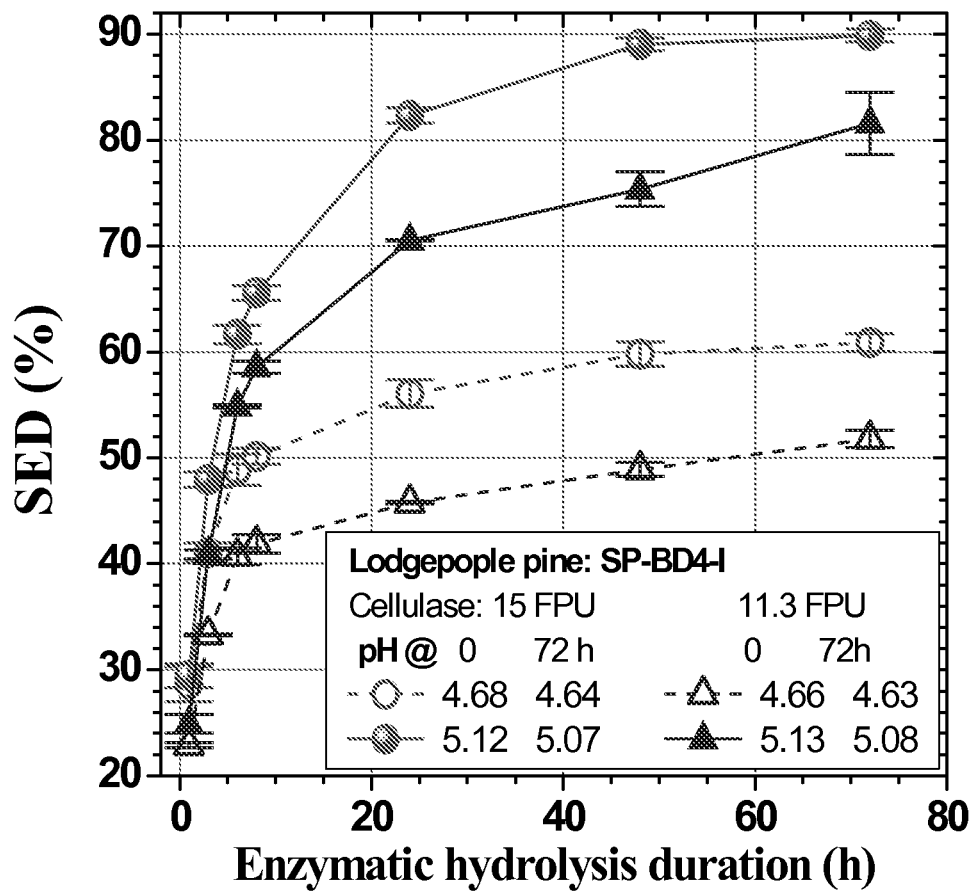
FIG. 5 illustrates that the enhancement in saccharification of a lignocellulose due to an increased pH can be maintained through a near-complete cellulose conversion using a mixture of CELLUCLAST 1.5L supplemented with Novozyme 188 according to some embodiments.

FIG. 5 illustrates that the enhancement in saccharification of a lignocellulose due to an increased pH can be maintained through a near-complete cellulose conversion, according to some embodiments. As shown in FIG. 5, the relative and absolute gains in substrate enzymatic digestibility (SED) were maintained when increasing from pH 4.67 (buffer pH 4.8) to pH 5.13 (buffer pH 5.5) for a SPORL pretreated lodgepole pine substrate through a near-complete cellulose conversion. The lignocellulosic substrate was SP-BD4-I, and the enhancements were significant and maintained through a near-complete cellulose conversion at a high CELLUCLAST 1.5 L loading of 15 FPU/glucan. The SED at 72 h was increased from approximately 50 to 80% and 60 to 90%, or by approximately 60 and 50% at CELLUCLAST 1.5L loadings of 11.3 and 15 FPU/glucan, respectively.

This result suggests that the amount, and thus costs, of cellulase loading can be reduced by approximately 40% by simply by adjusting the pH of the buffer solution from 4.8 to 5.5 for a SPORL pretreated lodgepole pine.

Example 5

An Enzyme Cocktail Containing Hemicellulase Enhances Saccharification in Lignocellulosic Substrates at an Elevated pH CTec2 is a cellulase cocktail that also contains hemicellulase. This example again shows that the enhanced enzymatic saccharification for CELLUCLAST 1.5L with use of a higher-than-recommended pH is also clearly observed using CTec2. This example also shows that lignin is the chemical component that affects the selection of pH in the enzymatic saccharification of a lignocellulosic material.

Figure 6:
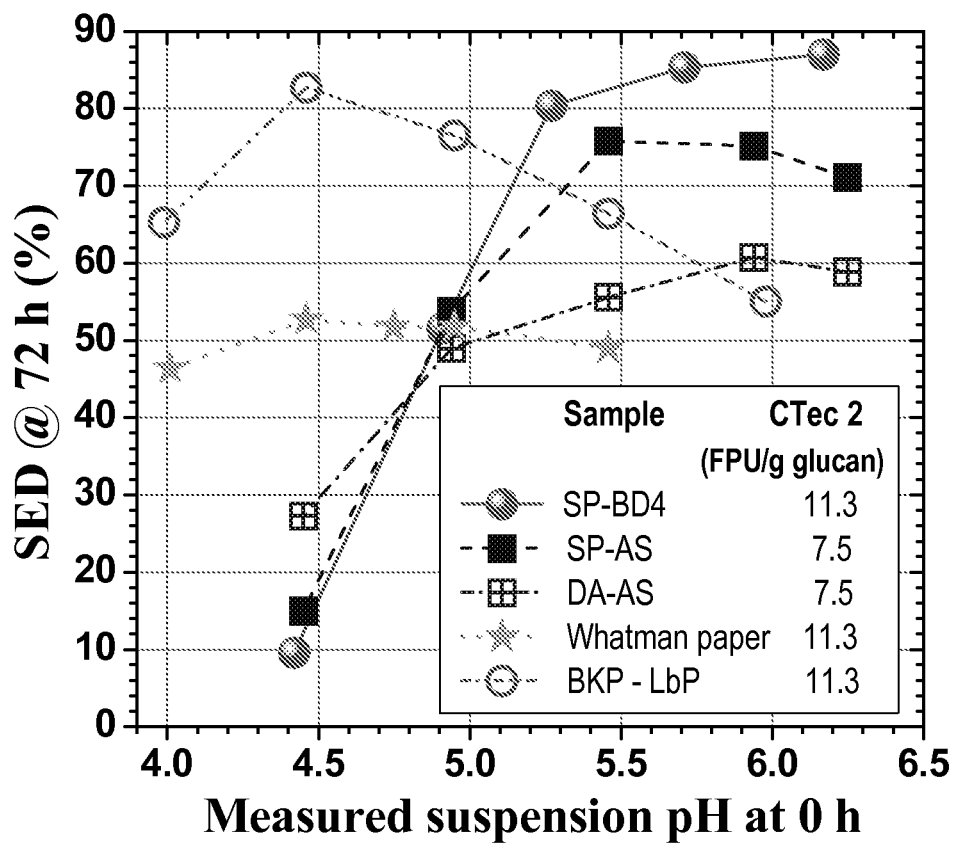
FIG. 6 illustrates an enzyme cocktail containing both cellulase and hemicellulase also has an enhanced saccharification when using a higher-than-recommended pH, according to some embodiments.

FIG. 6 illustrates an enzyme cocktail containing both cellulase and hemicellulase also has an enhanced saccharification when using a higher-than-recommended pH, according to some embodiments. In fact, at a hydrolysis temperature 50° C., the best pH was 6.0 or higher for the three lignocellulosic substrates tested. The best pH for the WHATMAN paper is around pH 4.5. A SPORL pretreated lodgepole pine substrate (SP-BD4) realized an SED increase from 51% to 87%, or by approximately 70%, when increasing pH from 4.9 to 6.2 (buffer solution 5.0 to 6.5). Enzymatic hydrolysis of a bleached kraft pulp of loblolly pine (BKF-LbP) was also conducted under different pH. BKF-LbP has lignin content 0.1% with glucan content of 80% and total hemicellulose (xylan and mannan) content of 15%. The best pH for enzymatic saccharification of the three lignocellulosic substrates (SP-BD4-I, SP-AS, DA-AS) ranged from 5.5-6.2, higher than the range of pH 4.5-5.0 for the two cellulosic substrates of WHATMAN paper and bleached loblolly pine (BKF-LbP). The best pH for the three lignocellulosic substrates appeared to range from 5.5-6.2 with CTec 2, which was higher than the best pH range of 5.2-5.7 with CELLUCLAST 1.5L. The CTec 2 was apparently a new and better enzyme to use than CELLUCLAST 1.5 L for these studies, particularly for the dilute acid pretreated aspen (DA-AS).

Table 6 compares the measured substrate suspension pH to the buffer solution pH for a variety of samples, the measured pH of the lignocellulosic substrate suspension measured at 0 h and 72 h enzymatic hydrolysis of the substrates, showing the use of these pH values in some embodiments.

Example 6

Hemicellulase Containing CTce2 can Enhance Saccharification in Lignocellulosic Substrates at an Elevated pH Another example using CTce2 was demonstrated here. The second set of four lignocellulosic substrates of lodgepole pine was pretreated by dilute acid and SPORL with different sulfite loadings and were enzymatically saccharified in a pH range of 4.5-6.0.

Figure 7:
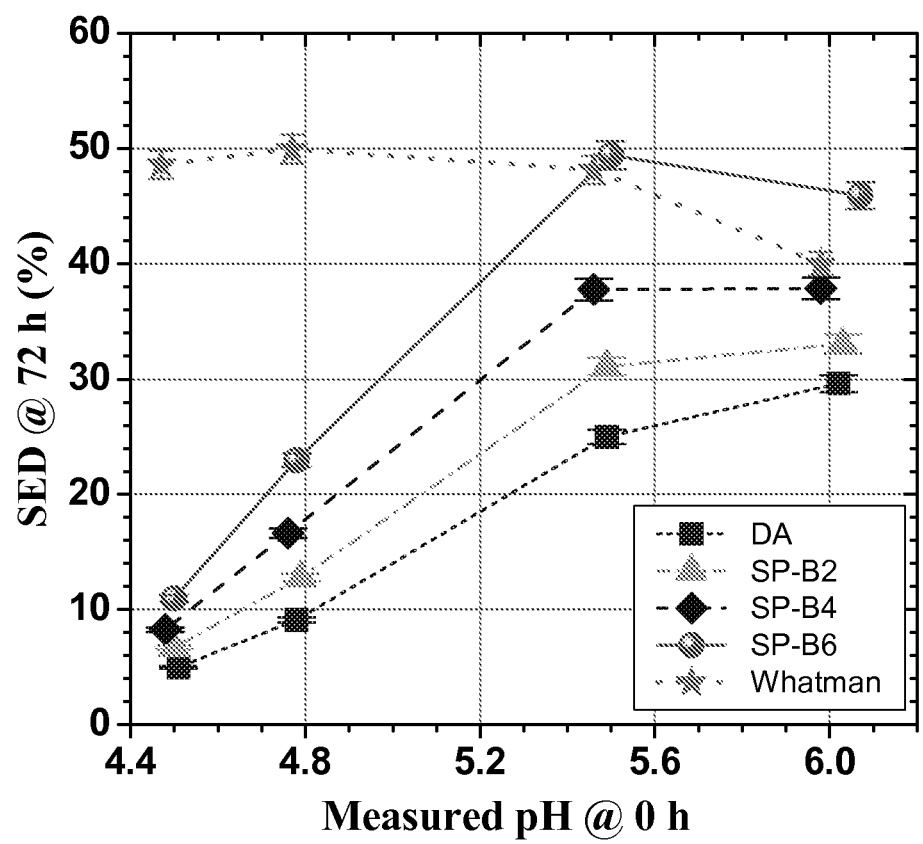
FIG. 7 illustrates the substrate enzyme digestibility (SED) of four lignocellulosic substrates of lodgepole pine in a pH range of about 4.5 to about 6.0 using CELLIC CTec2, according to some embodiments.

FIG. 7 illustrates the substrate enzyme digestibility (SED) of four lignocellulosic substrates in a pH range of about 4.5 to about 6.0, according to some embodiments. The results show the best pH to achieve maximum substrate enzymatic digestibility (SED) was between 5.5 and 6.0. Again, this is far-removed from, and contrary to, the teachings of Novozymes (the provider of CTce2), and the state-of-the-art knowledge, that pH 5.0 is the best pH to use for CTec2. The increase in SED was very significant, i.e., approximately by 50% for all four substrates, when pH was increased from 4.8 to 5.5. FIG. 7 uses the pH of the substrate suspension measured at 0 h of enzymatic hydrolysis in the x coordinate for plotting. Again the optimal pH for WHATMAN paper was found at pH 4.8.

Example 7

Non-Specific Enzyme Binding is Reduced in Lignin Residues at an Elevated pH, and a Reduction in the Nonspecific Binding Enhances Enzymatic Saccharification of Lignocelluloses This example shows the non-specific adsorption that occurs between lignin and enzymes. The change in pH, measured sulfonic acid group content, and zeta potential were measured and compared to the non-specific adsorption of the

TABLE 6

| Buffer solution pH | Measured substrate suspension pH at 0 and 72 h with Celluclast 1.5 L | | | | | | | | | | | |
|---|---|---|---|---|---|---|---|---|---|---|---|---|
| | SP-BD4-I | | SPH-FL | | KF-FL | | SP-AS | | SPH-AS | | DA-AS | |
| | 0 h | 72 | 0 | 72 | 0 | 72 | 0 | 72 | 0 | 72 | 0 | 72 |
| 4.0 | 3.91 | 3.90 | | | | | | | | | | |
| 4.5 | 4.39 | 4.37 | 4.37 | 4.37 | 4.50 | 4.50 | 4.38 | 4.37 | 4.37 | 4.38 | 4.38 | 4.38 |
| 4.8 | 4.67 | 4.64 | | | | | | | | | | |
| 5.0 | 4.80 | 4.76 | 4.86 | 4.82 | 4.99 | 5.00 | 4.88 | 4.86 | 4.87 | 4.84 | 4.86 | 4.86 |
| 5.5 | 5.13 | 5.08 | 5.31 | 5.25 | 5.54 | 5.53 | 5.33 | 5.30 | 5.33 | 5.25 | 5.32 | 5.28 |
| 6.0 | 5.54 | 5.35 | 5.70 | 5.56 | 6.27 | 6.13 | 5.78 | 5.68 | 5.79 | 5.62 | 5.74 | 5.65 |
| 6.5 | 5.94 | 5.61 | 5.93 | 5.78 | 6.87 | 6.61 | 6.04 | 5.88 | 6.08 | 5.85 | 5.99 | 5.86 |
| 7.0 | 6.35 | 5.88 | | | | | | | | | | |

| Buffer solution pH | With CTec2 | | | | | | | | | |
|---|---|---|---|---|---|---|---|---|---|---|
| | SP-BD4-I | | SP-AS | | DA-AS | | WHATMAN | | BKF-LbP | |
| | 0 | 72 | 0 | 72 | 0 | 72 | 0 | 72 | 0 | 72 |
| 4.0 | | | | | | | 4.01 | 3.92 | 3.99 | 3.92 |
| 4.5 | 4.42 | 4.39 | 4.43 | 4.39 | 4.45 | 4.40 | 4.46 | 4.41 | 4.46 | 4.39 |
| 4.8 | | | | | | | 4.75 | 4.69 | | |
| 5.0 | 4.91 | 4.78 | 4.95 | 4.88 | 4.94 | 4.86 | 4.95 | 4.90 | 4.95 | 4.90 |
| 5.5 | 5.27 | 5.21 | 5.47 | 5.32 | 5.46 | 5.31 | 5.46 | 5.39 | 5.46 | 5.42 |
| 6.0 | 5.71 | 5.52 | 5.83 | 5.67 | 5.94 | 5.62 | | | 5.98 | 5.85 |
| 6.5 | 6.17 | 5.74 | 6.19 | 5.76 | 6.25 | 5.63 | | | | |
| 7.0 | | | | | | | | | | | enzyme on the lignin. It should be appreciated that the term "adsorption" can be used interchangeably with the term "binding" for the purposes of this example. Interestingly, and of great commercial value, is that this example shows that a reduction in nonspecific binding of cellulase enhances enzymatic saccharification of lignocelluloses.

Figure 8:
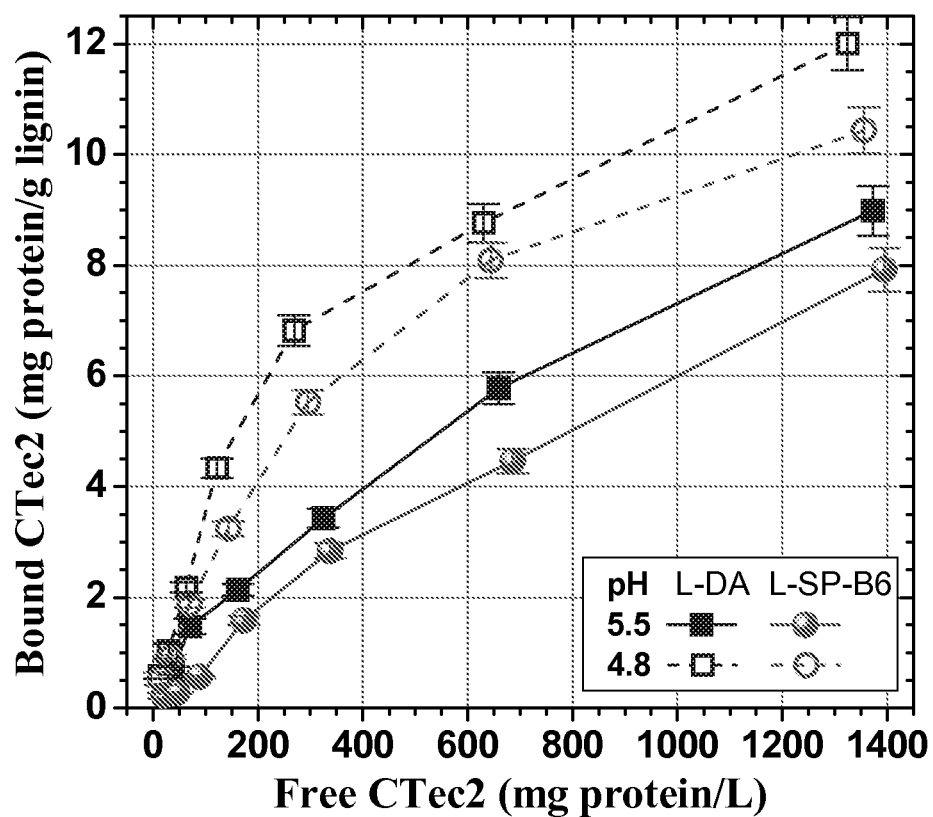
FIG. 8 illustrates isotherms of CTec2 adsorption by hydrolysis lignin residues of two lignocellulosic substrates at pH 4.8 and pH 5.5, respectively, according to some embodiments.

FIG. 8 illustrates isotherms of CTec2 adsorption by hydrolysis lignin residues of the lignocellulosic substrates at pH 4.8 and pH 5.5, according to some embodiments. The cellulase adsorption of the enzyme on the four hydrolysis lignin residues derived from the four pretreated lodgepole pine substrates was measured at increasing pH values. The CTec2 adsorption at pH 4.8, 50° C., and a CTec2 loading of 400 mg protein/L was asymptotic at about 30 min, suggesting an equilibrium point of 30 min. As such, 30 min was used as the fixed time for adsorption measurements. The isotherms of CTec2 adsorption by hydrolysis lignin residues L-DA and L-SP-B6 derived from substrates DA and SP-B6, respectively, at pH 4.8, 5.5, and 50° C. are shown. The adsorption was reduced at pH 5.5 compared to pH 4.8 with a wide variety of CTec2 loadings having a free CTec2 concentration ranging from 0-1400 mg protein/L. Although removed for clarity, similar results were also observed for the other two lignin residues L-SP-B2 and L-SP-B4.

Figure 9:
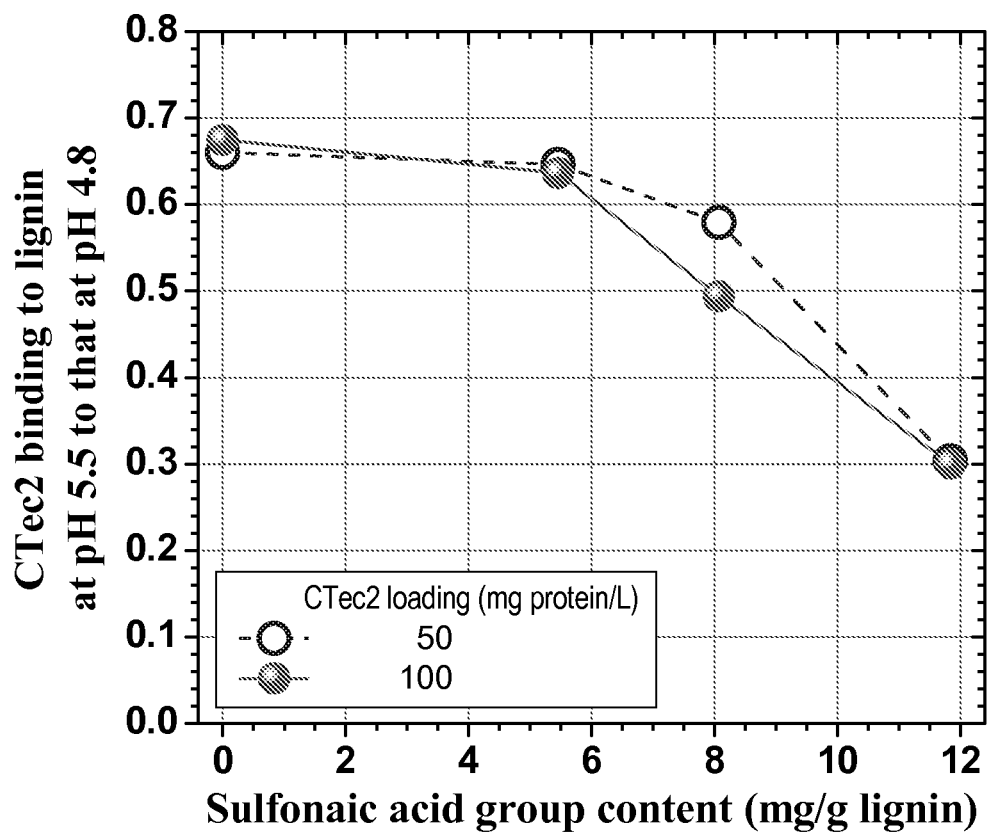
FIG. 9 illustrates the relative amount of enzyme bound to lignin at pH 5.5 as compared to pH 4.8 as a function of lignin sulfonic acid group content, according to some embodiments.

FIG. 9 illustrates the relative amount of enzyme bound to lignin at pH 5.5 as compared to pH 4.8 as a function of lignin sulfonic acid group content of the four hydrolysis lignin residues, according to some embodiments. The adsorption at pH 5.5 was approximately 70% of the adsorption at pH 4.8 for lignin L-DA, the lignin derived from the dilute acid pretreated substrate DA. Adsorption decreased as the lignin sulfonic acid group content increased. For example, the adsorption reduced to 30% for the lignin L-SP-B6 derived from substrate SP-B6 pretreated with 6% sodium bisulfite charge. The adsorptions at CTec2 loadings of 50 and 100 mg protein/L were almost identical for each of the four hydrolysis lignin residues.

Figure 10:
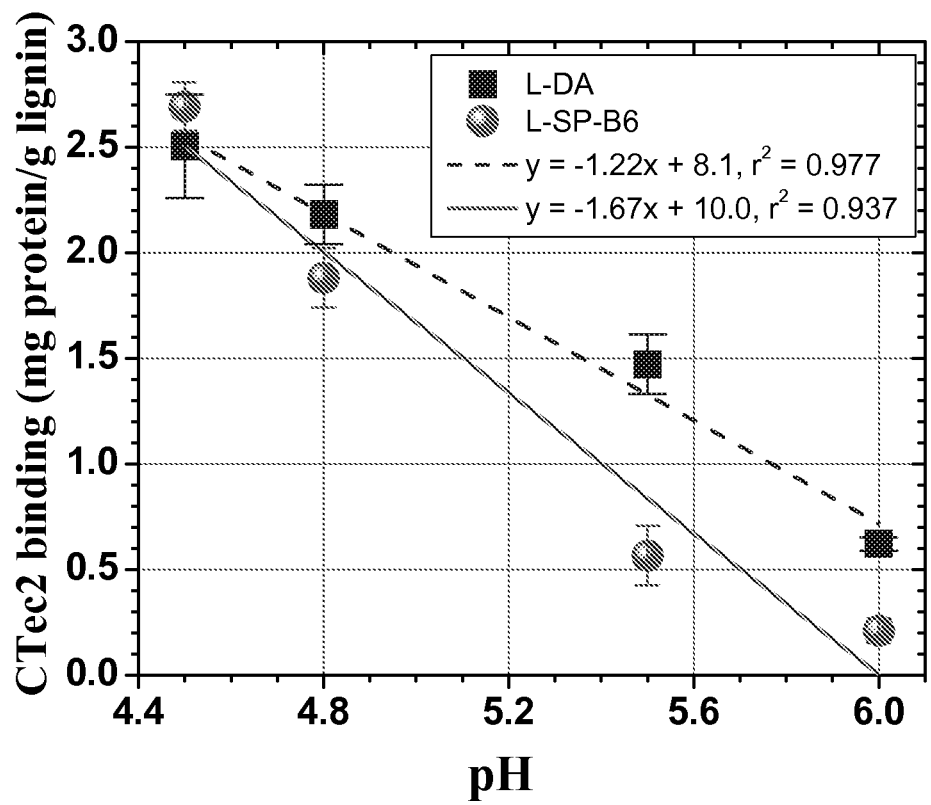
FIG. 10 illustrates linear relationship between the non-specific binding of an enzyme to lignin with change in pH, according to some embodiments.

FIG. 10 illustrates linear relationship between the nonspecific binding of an enzyme to lignin with change in pH, according to some embodiments. The reduction in adsorption was found to be linearly proportional to change in pH, and the nonspecific CTec2 binding to L-SP-B6 was near zero at pH 6.0. Although removed for clarity, similar linear reductions for the other two hydrolysis lignin residues L-SP-B2 and L-SP-B4 were also observed.

Figure 11:
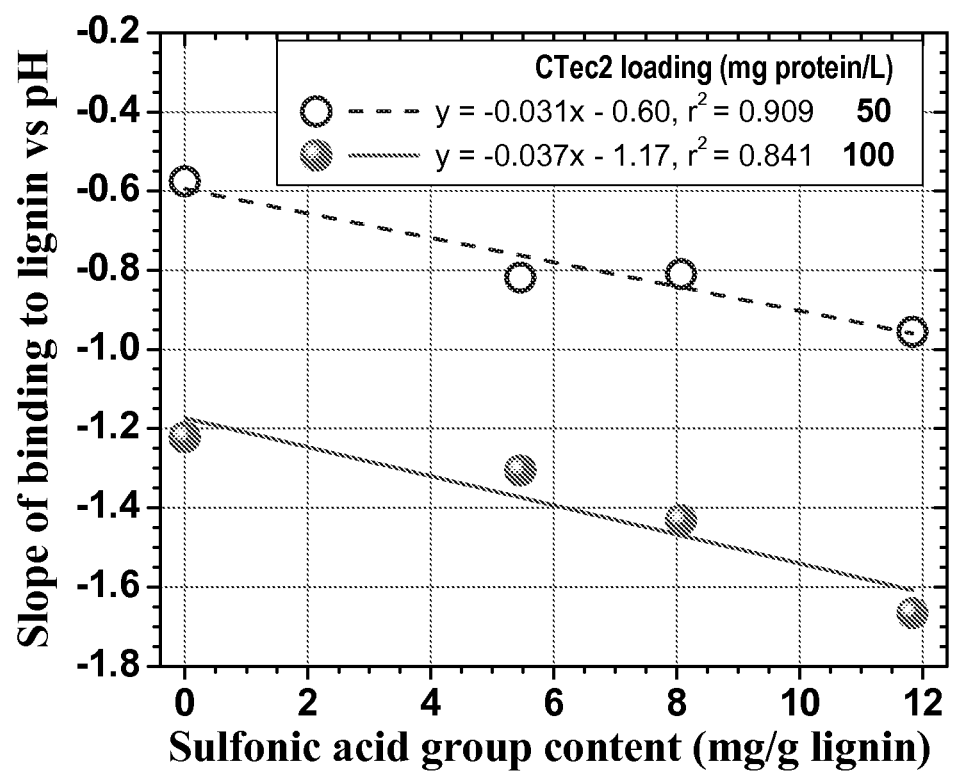
FIG. 11 illustrates a linear relationship between the amount of reduction in non-specific binding with respect to a change in pH and the lignin sulfonic acid group content, according to some embodiments.

FIG. 11 illustrates a linear relationship between the amount of reduction in non-specific binding with respect to a change in pH and the lignin sulfonic acid group content, according to some embodiments. The slopes (in absolute value) of the linear relationship for the four hydrolysis lignin residues were also found to increase linearly with lignin sulfonic acid group content.

The cellulase adsorption isotherms were found to fit well with a Langmuir model. The CTec2 binding parameters of maximum binding capacity a, affinity constant A, and binding strength $S = A\sigma$, along with and linear correlation coefficient $r^2$ are listed in Table 7. Maximum binding capacities, affinity constants, and binding strength of CTec2 on the four lignin residues at pH 4.8 are all higher than their corresponding value at pH 5.5. The ratio of the maximum binding capacity a at pH5.5 to that at pH 4.8, $\sigma_{pH5.5}/\sigma_{pH4.8}$ decreased rapidly as the lignin sulfonic acid group content increased, suggesting that the sulfonic acid group content is directly related to the non-specific adsorption.

TABLE 7

| Hydrolysis lignin residue | pH | Maximum binding capacity, $\sigma$ (mg/g lignin) | affinity constant, A (L/g protein) | Binding strength, $S = A * \sigma$ (mL/g lignin) | $r^2$ | $\sigma_{pH5.5}/\sigma_{pH4.8}$ |
|---|---|---|---|---|---|---|
| L-DA | 4.8 | 10.53 | 1.10 | 11.63 | 0.986 | 98.2% |
|  | 5.5 | 10.34 | 0.48 | 4.99 | 0.979 |  |
| L-SP-B2 | 4.8 | 15.61 | 0.72 | 11.31 | 1.000 | 67.1% |
|  | 5.5 | 10.48 | 0.53 | 5.54 | 0.992 |  |
| L-SP-B4 | 4.8 | 8.12 | 1.74 | 14.16 | 0.999 | 50.3% |
|  | 5.5 | 4.09 | 1.59 | 6.51 | 0.987 |  |
| L-SP-B6 | 4.8 | 7.71 | 1.27 | 9.82 | 0.983 | 41.7% |
|  | 5.5 | 3.22 | 0.80 | 2.56 | 0.889 |  |

Zeta potential was used to confirm that the pH-induces a surface charge on the lignin. A negatively charged surface, for example, is hydrophilic and unfavorable for binding to cellulase.

Figure 12:
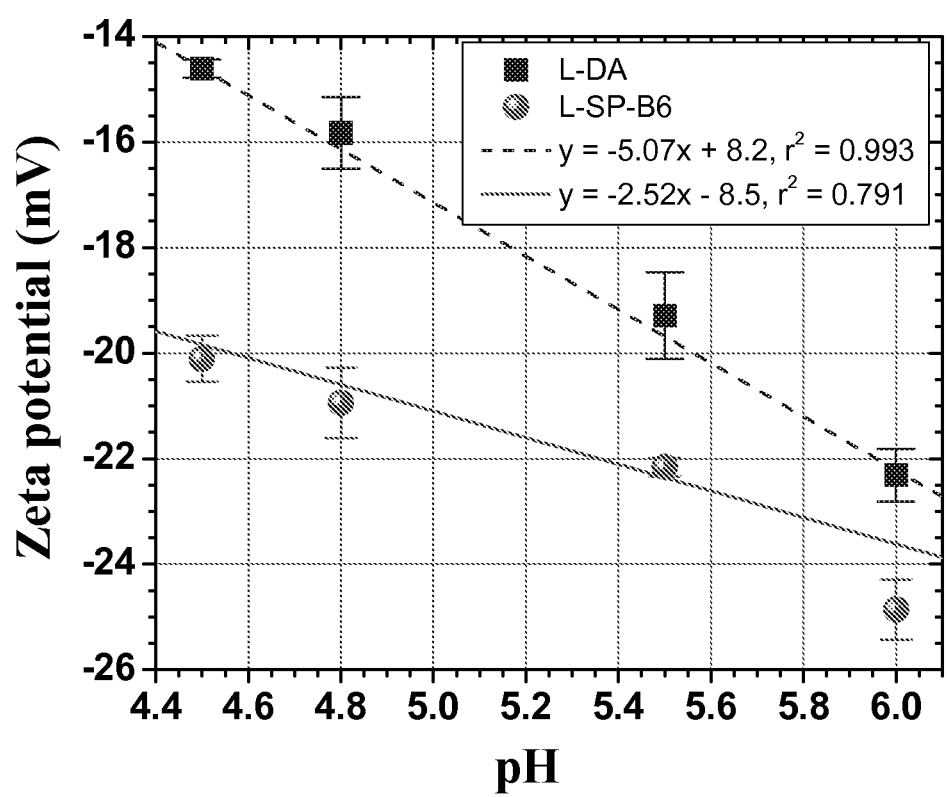
FIG. 12 illustrates relative zeta potential measurements as a function of pH in validation of an increase in negative surface charge of the lignin, according to some embodiments.

FIG. 12 illustrates relative zeta potential measurements as a function of pH in validation of an increase in negative surface charge of the lignin, according to some embodiments. The zeta potential of L-DA and L-SP-B6 increased linearly with pH ranging from pH 4.5-6.0, indicating that the lignin became more negatively charged as pH increased. Although removed for clarity, similar results were also observed for the other two lignin residues. The effect of pH in inducing a surface charge varied among the lignin samples.

One of skill will appreciate that electrostatic interactions between the enzyme and the lignin are also likely to contribute to the non-specific adsorption, and different enzymes will have different isoelectric points (pI). CTec2, for example, is an enzyme cocktail containing endoglucanase, exoglucanase and β-glucosidase. Most cellulases will have a pI≤5.5-6.0. Examples include EGI (Cel7B, pI 3.9, 4.5, 4.7), EGII (Cel5A, pI 4.2, 5.5), CBHI (Cel7A, pI 3.6-3.9), β-glucosidase (Aspergillus sp., pI 4.0), and CBHIII (Cel6A, pI 5.2, 5.9). These enzymes will have negative surface charges at elevated pH 5.5-6.0 (>pI) and less affinity to lignin due to an electrostatic repulsion force. Only β-glucosidase I (pI 8.5) and EG III (Cel12A, pI 6.8-7.4) have a very high pI>6.0. As such, it should be appreciated that these enzymes can be expected to have a positive charge at a pH range of 5.5-6.0. One of skill should take into account the risk of non-specific adsorption during enzyme selection. A high pH provided more flexibility to reduce enzyme loadings for most enzymes with lower pI than the pH used for hydrolysis due to the electrostatic repulsion.

Figure 13:
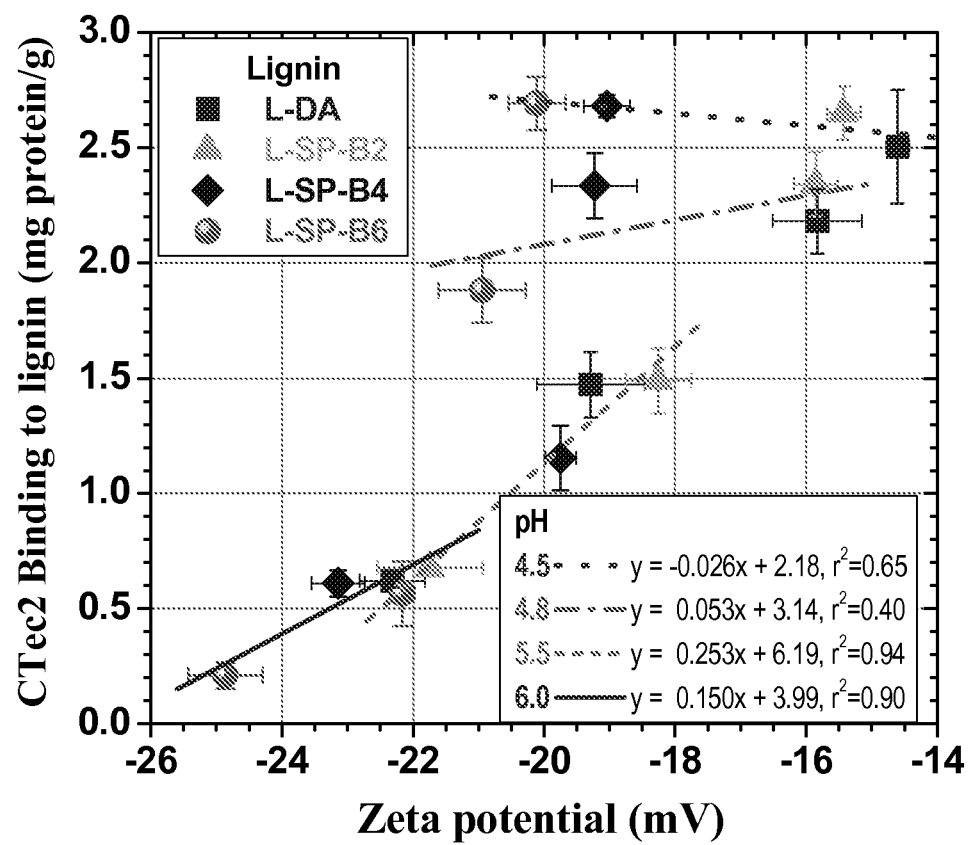
FIG. 13 illustrates linear relationships between the non-specific binding of an enzyme and the zeta potential of lignin for the four lignocellulosic substrates at each pH tested, according to some embodiments.

FIG. 13 illustrates linear relationships between the non-specific binding of an enzyme and the zeta potential of lignin for the four lignocellulosic substrates at each pH tested, according to some embodiments. The results relate pH to adsorption as a function of zeta potential, inferring the relationship of the lignin sulfonic acid group content to nonspecific binding of the enzyme on the lignin. Adsorption was not significantly affected by lignin sulfonation at low pH values of 4.5 and 4.8, as shown by the slopes of the regression lines being near zero. This may be partly due to the lack of significant surface hydrophilicity due to low lignin surface charges at the low pH. An electrostatic repulsion may therefore be lacking between the lignin and the cellulase enzyme, as such most enzymes can have low negative, near zero, or slightly positive surface charges at low pH. Most cellulase enzymes, for example, have a pI that is not very different from 4.5 and 4.8. At elevated pH values of 5.5 and 6.0, however, the adsorption decreased rapidly with zeta potential as shown by the slopes of the lines. This may be due to an increased lignin surface hydrophilicity due to increased negative charges and electrostatic repulsion most cellulase enzymes at the elevated pH. While not intending to be bound by any theory or mechanism of action, both pH-induced lignin surface hydrophilicity and pH-induced enhanced electrostatic repulsion between lignin and enzymes appear to contribute to reductions in nonspecific binding of cellulase to lignin.

Figure 14:
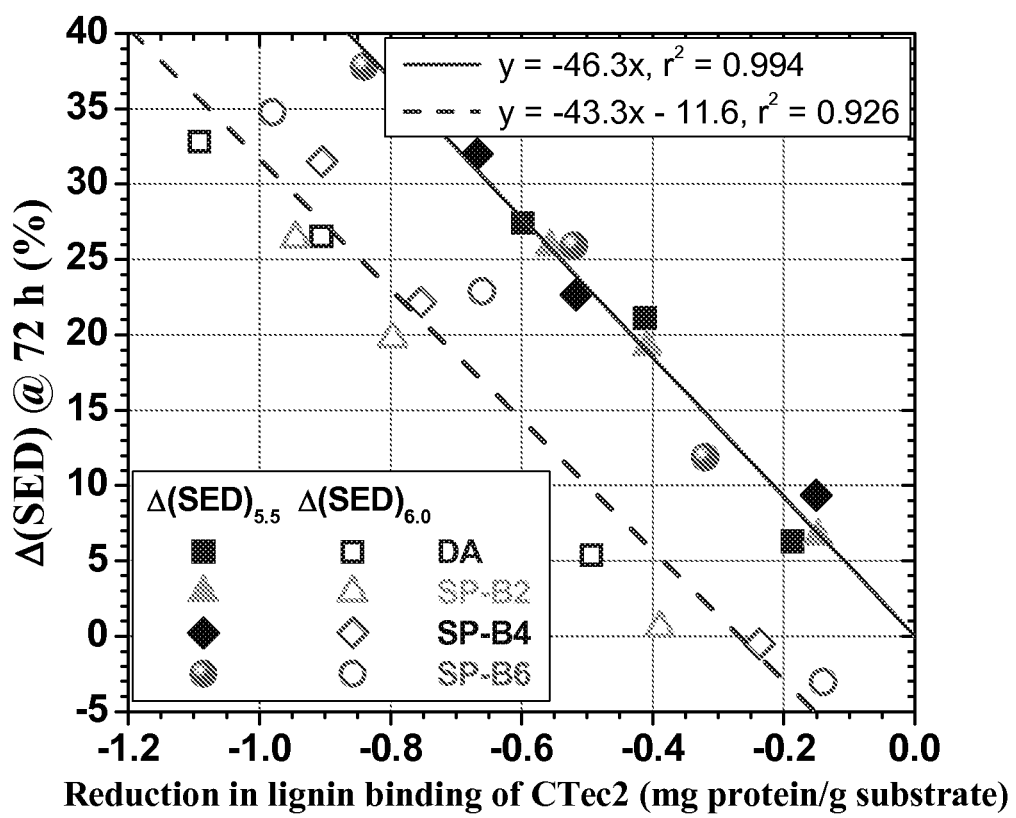
FIG. 14 shows that a reduction in nonspecific binding of cellulase enhances enzymatic saccharification of lignocelluloses at elevated pH, according to some embodiments.

FIG. 14 shows that a reduction in nonspecific binding of cellulase enhances enzymatic saccharification of lignocelluloses at elevated pH, according to some embodiments. A percentage increase in substrate enzyme digestibility (SED) of four lignocellulosic substrates at a pH range of about 4.5 to about 6.0 is shown, where gains in enzymatic saccharification were plotted against reductions in non-specific lignin binding of CTec2 to lignin. The $\Delta(SED)_{5.5}$ was calculated by subtracting SED at pH 4.5, 4.8 form SED at pH 5.5, and SED at pH 4.5 from SED at pH 4.8. The $\Delta(SED)_{6.0}$ was calculated by subtracting SED at pH 4.5, 4.8, and 5.5 form SED at pH 6.0. Interestingly, the results show that $\Delta(SED)_{pH}$ falls into excellent linear fits that shift with pH, and this appears to hold regardless of pretreatment (DA and SPORL) or lignin structure. The downward shift of the linear fit relative to pH at a given reduction in binding shows that increasing pH over 5.5 did not produce a benefit, even though the adsorption was further reduced (FIG. 10). While not intending to be bound by any theory or mechanism of action, this is likely because the cellulase activity is reduced at the higher pH as shown by the hydrolysis data of WHATMAN Paper (pure cellulose) in FIGS. 6 and 7.

Example 8

The Addition of a Lignosulfonate Enhances Enzymatic Hydrolysis of a Lignocellulose This example shows that addition of a lignosulfonate enhances enzymatic hydrolysis of a lignocellulose at pH 4.8. A SPORL pretreatment hydrolysate from lodgepole pine (L-BD4-T85-3) was first neutralized using NaOH to pH 4.8 and then applied to enzymatic hydrolysis of a SPORL pretreated lodgepole pine solid substrate (S-SP-BD4-II).

Figure 15:
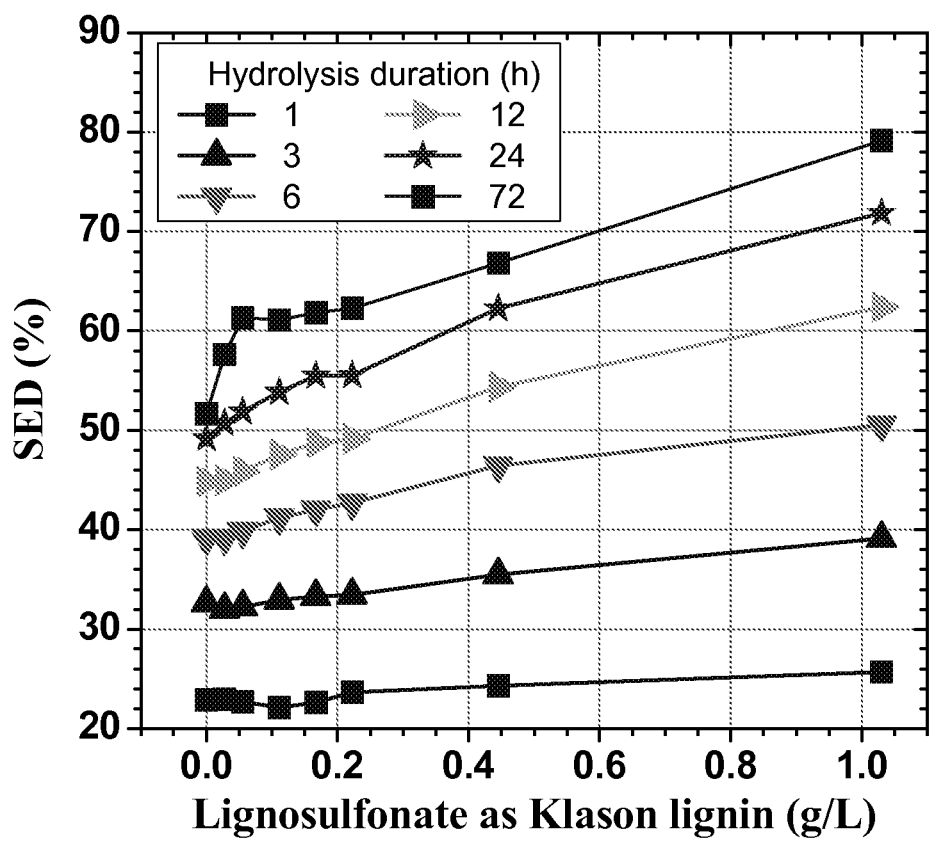
FIG. 15 shows that the addition of a lignosulfonate enhances hydrolysis of a lodgepole pine at pH 4.8, according to some embodiments.

FIG. 15 shows that the addition of a lignosulfonate enhances hydrolysis of a lodgepole pine at pH 4.8, according to some embodiments. The cellulose conversion of S-SP-BD4-II represented by SED increased linearly with the increase in lignosulfonate concentration in the mixed hydrolysate. The SED increased from approximately 49% to 72% at 24 h by applying lignosulfonate at 1.0 g/L (as Klason lignin). The amount of glucose in L-BD4-T85-3 was subtracted from the measured glucose concentration in the mixed hydrolysate for calculating SED. Increasing the lignosulfonate concentration to approximately 1.0 g/L as Klason lignin, equivalent to lignin concentration in the whole slurry of the pretreated material when hydrolyzed at 2% water insoluble solids, the SED was increased from 52% to 78% or by 50% at 72 h.

Three SPORL-pretreatment hydrolysates, i.e., L-BD4-T85-1, L-BD4-T85-2, L-BD4-T85-3, obtained from three pretreatments with different pretreatment times (Table 3) were used to further verify the positive effects of adding lignosulfonate. Both NaOH and $Ca(OH)_2$ were used to neutralize the hydrolysates to pH 4.8 before application.

Figure 16:
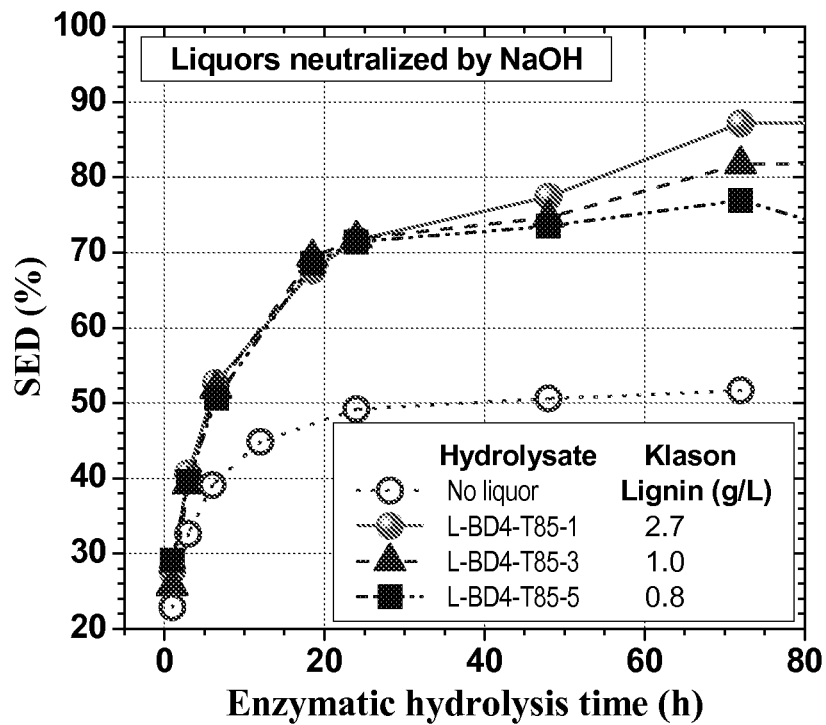
FIGS. 16A and 16B illustrate that the substrate enzymatic digestibility (SED) can increase by over 50% through application of a pretreatment hydrolysate containing a lignosulfonate, according to some embodiments.
Figure 16:
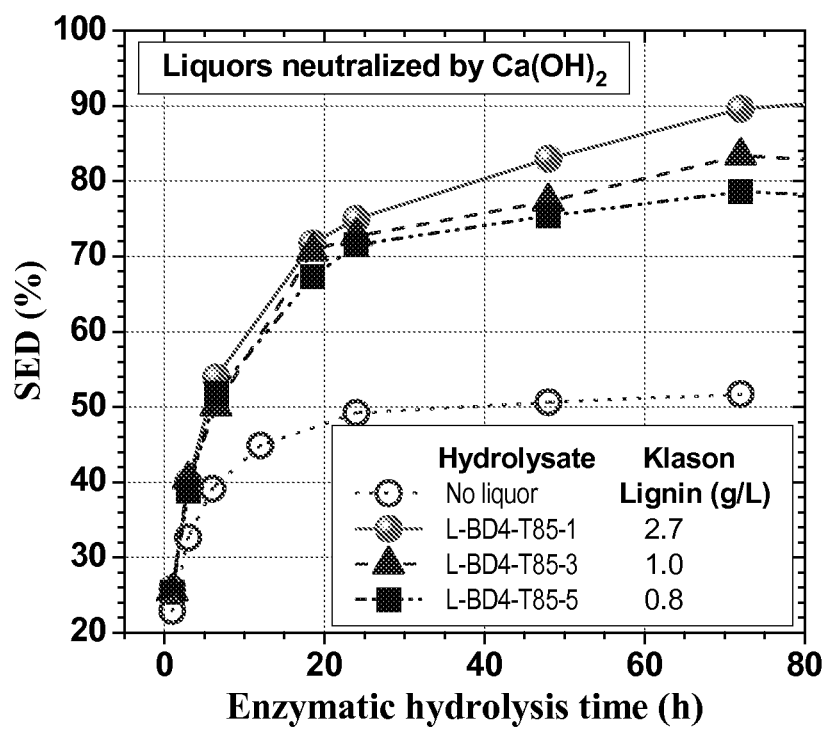

FIGS. 16A and 16B illustrate that the substrate enzymatic digestibility (SED) can increase by over 50% through application of a pretreatment hydrolysate containing a lignosulfonate, according to some embodiments. The SED of a SPORL-pretreated lodgepole pine, S-SP-BD4-II, increased by over 50% when any of the pretreatment hydrolysate was applied. The hydrolysate with shortest pretreatment of 5 min, the hydrolysate of L-BD4-T85-1, with the highest lignosulfonate concentration of 2.7 g/L as Klason lignin produced highest gain in enzymatic saccharification. As shown in FIG. 16A, the SED at 72 h was increased from approximately 52% to 87%, or by 67%. As shown in FIG. 16B, the hydrolysate with the longest pretreatment of 45 min, the hydrolysate of L-BD4-T85-5, with lowest lignosulfonate concentration of 0.8 g/L as Klason lignin produced the smallest gain in SED at 72 h of 78%.

Example 9

The Data Suggests that the Cellulase Costs of a Near-Complete Conversion of a Lodgepole Pine can be Reduced by About 46% Using a SPORL Pretreatment, Addition of a Lignosulfonate, and an Increased pH for the Enzymatic Hydrolysis This example shows that addition of a lignosulfonate enhances enzymatic hydrolysis of a lodgepole pine at pH 5.3. A SPORL pretreatment hydrolysate from lodgepole pine (L-BD4-T85-3) was first neutralized to pH 5.3 and then applied to enzymatic hydrolysis of a SPORL pretreated lodgepole pine solid substrate (SP-BD4-II). A concentration of 11.5 g/L lignosulfonate was used.

Figure 17:
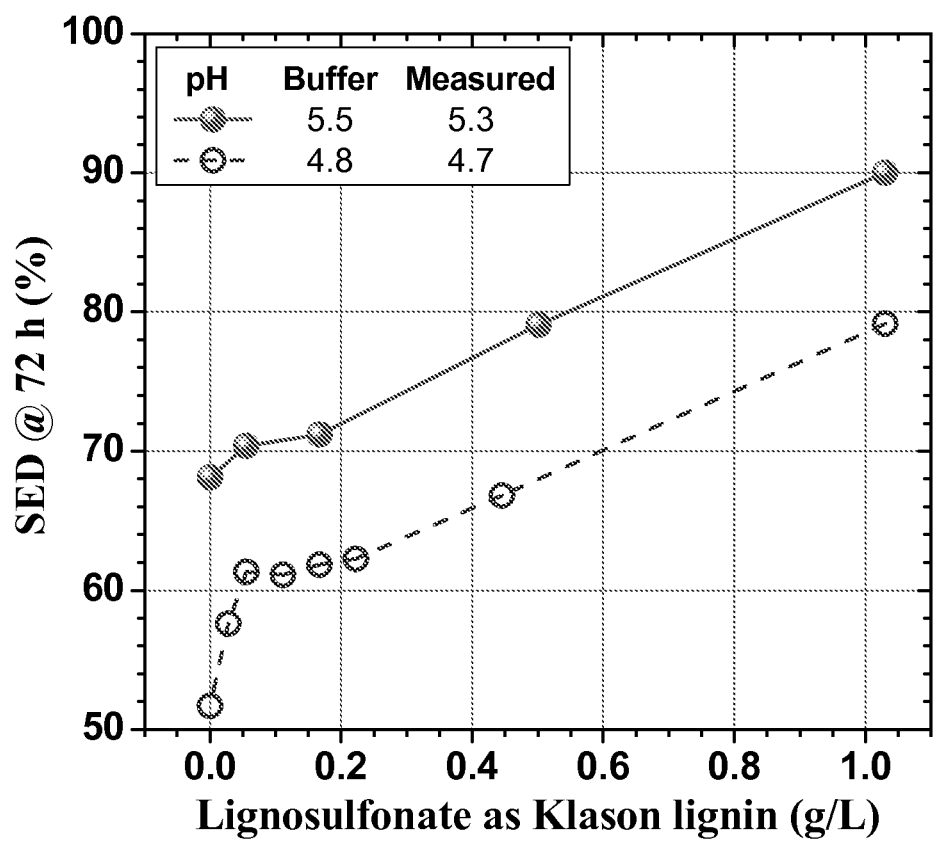
FIG. 17 shows that the addition of a lignosulfonate enhances hydrolysis of a lodgepole pine at pH 5.3 using CELLUCLAST 1.5L supplemented with Novozyme 188, according to some embodiments.

FIG. 17 shows that the addition of a lignosulfonate enhances hydrolysis of a lodgepole pine at pH 5.3 using CELLUCLAST 1.5L supplemented with Novozyme 188, according to some embodiments. The SED at 72 h increases linearly with lignosulfonate concentration in the mixed hydrolysate, and an additional gain in SED at 72 h of 10% was achieved when increasing the pH to 5.3 (buffer solution pH 5.5). The application of lignosulfonate at elevated pH furthers enhances enzymatic hydrolysis of lignocelluloses. An SED of 90% can be achieved at a CELLUCLAST 1.5L loading of only 13 FPU/g glucan after 72 h of enzymatic hydrolysis for the SPORL-pretreated softwood substrate, SP-BD4-II. This was a surprising result, as the SED of the corresponding control run (pH 4.8 without lignosulfonate) was only 51%. A similar substrate produced from the same batch of lodgepole pine (BD4) wood chips and identical SPORL-pretreatment conditions needed a cellulase loading of 24 FPU/g glucan to achieve 90% cellulose conversion without the application of pretreatment hydrolysate that containing lignosulfonate (X Luo, Ind Eng Chem Res 49(17):8258-8266(2010), hereby incorporated herein by reference in its entirety).

This data suggests that a 46% savings in cellulase loading is realized using the addition of lignosulfonate and the elevated pH for lodgepole pine. As noted earlier, one of skill will also appreciate the process benefit that the increased pH is also favorable for yeast fermentations and can simplify processing.

Example 10

Addition of a Pretreatment Hydrolysate Containing a Lignosulfonate Enhances Enzymatic Hydrolysis of an Aspen Pine at pH 5.5

This example shows that addition of a lignosulfonate enhances enzymatic hydrolysis of pretreated aspen at pH 5.5. A SPORL pretreatment hydrolysate from lodgepole pine (L-BD4-T85-3) was first neutralized to pH 5.5 and then applied to enzymatic hydrolysis of two aspen solid substrates (DA-AS and SP-AS). A lignosulfonate concentration of 1.0 g/L as Klason lignin was used.

Figure 18:
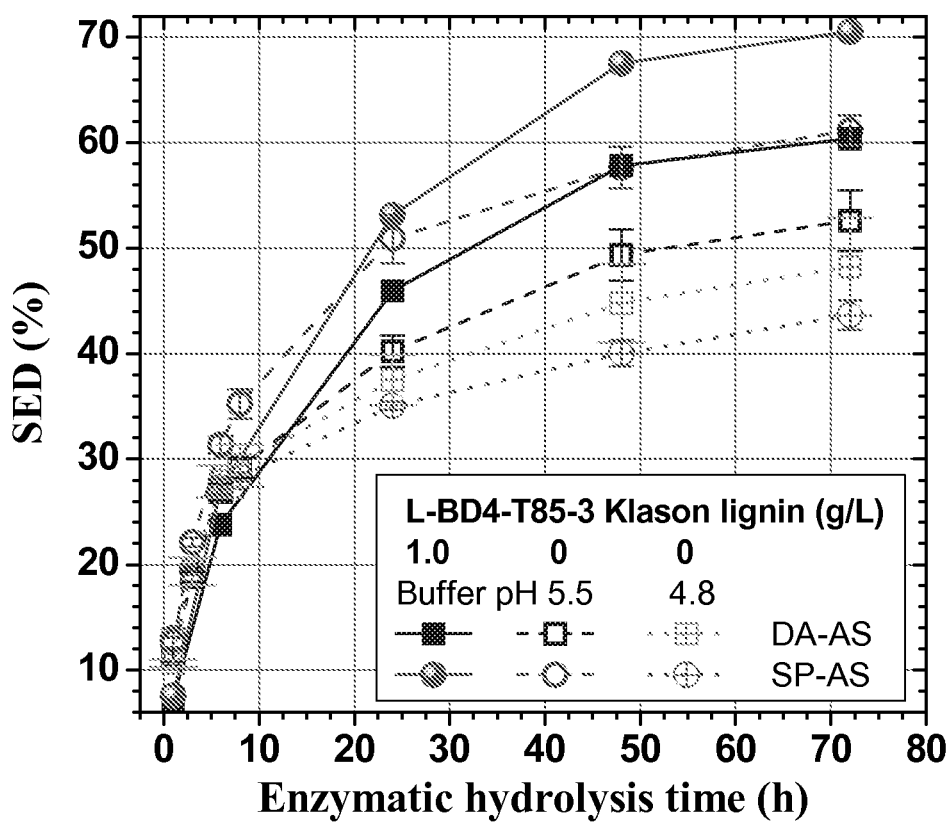
FIG. 18 shows that the addition of a lignosulfonate enhances hydrolysis of the two aspen substrates at pH 5.5, according to some embodiments.

FIG. 18 shows that the addition of a lignosulfonate enhances hydrolysis of the two aspen substrates at pH 5.5, according to some embodiments. The SED gains reinforce that the high pH alone enhances enzymatic saccharification, and the lignosulfonate alone enhanced enzymatic hydrolysis after 24 hours.

The SED of both substrates after 24 hours were further enhanced at elevated buffer pH 5.5. When compared with the control run using buffer solution pH of 4.8 without the application of pretreatment hydrolysate (L-BD4-T85-3), the SED values at 72 h increased by 25% and 62% for the DA-AS and SP-AS, respectively, and the pH effect was more pronounced for the SPORL-pretreated sample.

Example 11

Addition of a Commercial Lignosulfonate Enhances Enzymatic Hydrolysis of Pretreated Aspen and Lodgepole Pine at pH 5.5

This example shows that an off-the-shelf, commercial lignosulfonate can be used to enhance enzymatic hydrolysis. A commercial lignosulfonate (D748, LignoTech USA, Rothschild, Wis.) was applied to enzymatic hydrolysis of two pretreated aspen substrates, DA-AS and SPH-AS, and a pretreated lodgepole pine SP-BD4-II at a lignosulfonate concentration of 10 g/L and elevated buffer solution pH of 5.5.

Figure 19:
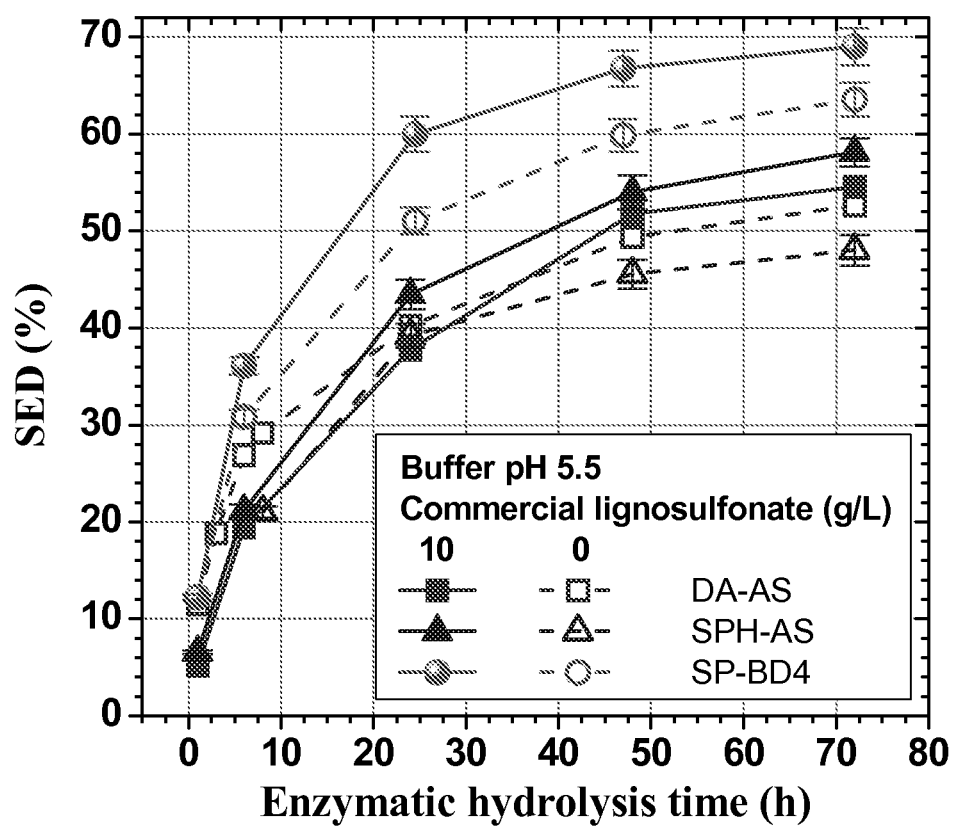
FIG. 19 shows that an off-the-shelf, commercial lignosulfonate can be used to enhance enzymatic hydrolysis of aspen and lodgepole pine, according some embodiments.

FIG. 19 shows that an off-the-shelf, commercial lignosulfonate can be used to enhance enzymatic hydrolysis, according some embodiments. The SED at 72 of the SPORL pretreated aspen (using sodium bisulfite only) can be increased by 23% with the application of the commercial lignosulfonate. A slight increase in SED was also observed from the dilute acid pretreated aspen, DA-AS. The commercial lignosulfonate was equally effective to increase enzymatic hydrolysis of lignocelluloses.

Example 12

The Use of a Lignosulfonate Additive and a pH of 5.5 Provides a High Titer and High Yield Ethanol Production This example shows that of a lignosulfonate additive and a pH of 5.5 provides a high titer and high yield ethanol production process. A process similar to FIG. 2B but with yeast fermentation was used to produce an ethanol yield of 285 L/ton wood at 47.4 g/L with a cellulase (CTec2) loading of only 9 FPU or 0.06 mL/g wood at a processing total solids content of up to 20%. This is a surprising result, as the use of high solids will usually reduce yield. One of skill will appreciate that this is a very significant improvement over the state-of-the-art.

Microorganism and Culture

*Saccharomyces cerevisiae* YRH400 was used, and is an engineered fungal strain for xylose fermentation with the needed genes integrated into the genome. The strain was grown at 30° C. for 2 days on YPD agar plates containing 10 g/L yeast extract, 20 g/L peptone, 20 g/L glucose, and 20 g/L agar. A colony from the plate was then transferred by loop to a liquid YPD medium in a flask. The *S. cerevisiae* YRH400 seed was cultured for 2 days at 30° C. with agitation at 90 rpm on a shaking bed incubator (Thermo Fisher Scientific, Model 4450, Waltham, Mass.). The harvested broth was used to inoculate the fermentation culture.

Substrate Production by SPORL

The lodgepole pine, BD4, was pretreated using sulfite pretreatment to overcome recalcitrance of lignocellulose (SPORL). See Zhu J Y et al., Bioresource Technology, 100 (8):2411-2418(2009); and, Wang G S, et al. Biotechnology Progress 25(4):1086-1093(2009), hereby incorporated herein by reference in its entirety. The pretreated wood chips were disk milled with the pretreatment spent liquor hydrolysate using disk plates having a pattern of D2B-505 and a disk plate gap of 1.0 mm.

Pretreatment Spent Liquor Hydrolysate Concentration and Conditioning

The spent liquor hydrolysate was concentrated to remove excess water added in disk milling using a vacuum rotary evaporator (Rotavapor-R type WB, Buchi, Switzerland) at about 52° C. to avoid sugar degradation. The volumetric and mass concentration ratios of 6.25 and 5.42, respectively, were determined based the initial and final liquor volumes and weights. The pH of the concentrated liquor was adjusted using lime. When combined with the acidic solid fraction, this led to a final pH of greater than 5.5. Table 8 profiles the pretreatment spent liquor hydrolysate.

TABLE 8

|  | Unconcentrated liquor | Concentrated liquor (Measured) | Concentrated liquor (Calculated) | Δ (%) |
| --- | --- | --- | --- | --- |
| Volume (mL) | 1000 | 160 | NA | |
| Weight (g) | 1000 | 184.5 | NA | |
| Density (g/mL) | 1.03 | 1.12 | 1.188 | −5.72 |
| Total solids (%) | 6.5 | | | |
| Arabinose (g/) | 0.92 ± 0.02 | 5.62 ± 0.37 | 5.76 | −2.43 |
| Glactose (g/L) | 2.27 ± 0.05 | 13.03 ± 0.31 | 14.18 | −8.11 |
| Glucose (g/L) | 5.85 ± 0.34 | 36.20 ± 1.58 | 36.56 | −0.98 |
| Xylose (g/L) | 2.99 ± 0.12 | 17.95 ± 0.63 | 18.71 | −4.06 |
| Mannose (g/L) | 8.01 ± 0.20 | 47.04 ± 1.33 | 50.06 | −6.03 |
| Furfural (g/L) | 0.26 ± 0.01 | 0.51 ± 0.02 | 1.63 | −68.71 |

TABLE 8-continued

|  | Unconcentrated liquor | Concentrated liquor (Measured) | Concentrated liquor (Calculated) | Δ (%) |
|---|---|---|---|---|
| HMF (g/L) | 1.24 ± 0.08 | 6.38 ± 0.49 | 7.75 | −17.68 |
| Acetic acid (g/L) | 2.67 ± 0.13 | 6.62 ± 0.19 | 16.69 | −60.34 |

Fed-Batch Saccharification Solids and Combined Fermentation with Pretreatment Liquor Different amounts of concentrated and conditioned liquor were used in 7 fed-batch quasi-simultaneous saccharification and combined fermentation (qSSCombF) experiments as listed in Table 9.

solids were liquefied by visual observation. The fermentation broth samples were centrifuged at 12,000 rpm for 5 min, and the supernatants were stored at −16° C. for later analyses of ethanol, sugars, and inhibitors. Duplicate saccharification and fermentation experiments were conducted for select Runs 1, 2 and 5 to verify repeatability.

TABLE 9

| Run | Total dry solids (g); wet weight (g) of conc liquor 0 h | Amount of unwashed solid substrate fed at each time point: dry weight (g); wet weight (g) | | | | Initial total solids (%) 0 h | Calc'd final total solids (%) 96 h |
|---|---|---|---|---|---|---|---|
| | | 0 h | 24 h | 48 h | 72 h | 96 h | | |

| Run | 0 h | 0 h | 24 h | 48 h | 72 h | 96 h | 0 h | 96 h |
|---|---|---|---|---|---|---|---|---|
| 1 | 0.84; 2.38 | 2.5; 10.6 | 1.42; 6.0 | 1.42; 6.0 | 0; | 0; | 13.4 | 16.7 |
| 2 | 1.46; 4.15 | 2.5; 10.6 | 1.42; 6.0 | 1.42; 6.0 | 0; | 1.42; 5.0 | 15.9 | 19.2 |
| 3 | 1.31; 3.71 | 2.5; 10.6 | 1.77; 7.5 | 0; | 1.77; 7.5 | 0; | 15.2 | 18.5 |
| 4 | 1.46; 4.15 | 2.5; 10.6 | 2.12; 9.0 | 0; | 0; | 2.12; 9.0 | 15.9 | 19.3 |
| 5 | 1.26; 3.56 | 3.0; 12.7 | 1.42; 6.0 | 0; | 1.42; 6.0 | 0; | 16.4 | 18.8 |
| 6 | 1.42; 4.02 | 3.0; 12.7 | 1.77; 7.5 | 0; | 0; | 1.77; 7.5 | 17.0 | 19.5 |
| 7 | 1.57; 4.45 | 3.0; 12.7 | 2.12; 9.0 | 0; | 0; | 2.12; 9.0 | 17.6 | 20.1 |

To demonstrate (1) application of SPORL pretreatment spent liquor as a hydrolysate that contains lignosulfonate and (2) enzymatic saccharification at an elevated pH, such as pH 5.5 or higher, the liquor was first added with a fixed amount of pretreated solid substrate and the mixture was then added lime to adjust its pH to 6.2. An acetic acid/sodium acetate buffer of pH 5.5 (50 mM) was added into the pH 6.2 mixture to conduct enzymatic hydrolysis at a pH of about 5.5-6.0. Commercial cellulase enzyme CTec2 loading was only 12 FPU/g od unwashed solid substrate, or 9 FPU or 0.06 mL/g untreated wood. Hydrolysis was done in 125-mL flasks on a shaker/incubator (Thermo Fisher Scientific, Model 4450, Waltham, Mass.) at 50° C. and 200 rpm for 4 h to partially liquefy the solid substrate for convenient dosing. The hydrolysate mixture was cooled to room temperature and then inoculated with 2 mL of yeast seed. After inoculation, the mixture was incubated at 35° C. and 100 rpm. The pretreated solids were batch fed periodically according to the schedule listed in Table 9. The amount fed and feeding time varied so that new feeding was made only after the existing solids were liquefied. The fermentation was terminated after 168 h. The fermentation broth was sampled periodically. Sampling was always taken just before feedings and only when pretreated Analytical Methods To determine monomeric sugar and inhibitors in the unwashed pretreated acidic solid fraction, the solid substrate was diluted to 4% total solids consistency and mixed. The diluted solution was centrifuged, and the supernatant was analyzed.

Ethanol was measured using an HPLC system (model L-2490, Hitachi High-Technologies Corporation, Japan) equipped with a BIORAD (Hercules, Calif.) AMINEX HPX-87H column (300×7.8 mm) operated at 55° C. Dilute sulfuric acid solution of 5 mM was used as eluent at a flow rate of 0.3 mL/min. Sample injection volume was 20 μL. Refractive index detection was used to quantify ethanol through calibration. Samples were diluted in deionized water, and then filtered through PREPSEP C18 (Fisher Scientific) filters prior to injection.

Wood Component Recovery Through SPORL Pretreatment

The wet weight and moisture content of the initial wood chips, SPORL pretreated unwashed acidic solid fraction, and pretreatment spent liquor hydrolysate were listed in Table 10.

TABLE 10

|  | Untreated wood | Unwashed solid substrate[a] | Unconcentrated liquid (spent liquor)[a] | Total recovery (%) |
|---|---|---|---|---|
| Total mass (kg) | 2.27 | 6.29; | 6.23; | |
| Moisture (%) | 11.7 | 76.4; | 93.5; | |
| Total solids (kg)[b] | 2.00 | 1.48; 74.2% | 0.40; 20% | 94.5 |
| Klason lignin (%) | 28.6 | 23.4; 81.7% | 5.2; 18.3% (by balance) | 100.0 |
| Arabinan (%) | 1.7 | 0.6 ± 0.00; 34.2% | 0.3; 17.8% | 52.0 |
| Galactan (%) | 2.9 | 1.6 ± 0.04; 54.0% | 0.7; 25.5% | 79.5 |
| Glucan (%) | 41.9 | 36.6 ± 1.01; 87.4% | 1.5; 3.7% | 91.1 |
| Xylan (%) | 5.5 | 2.9 ± 0.09; 52.5% | 0.9; 16.9% | 69.4 |

TABLE 10-continued

|  | Untreated wood | Unwashed solid substrate[a] | Unconcentrated liquid (spent liquor)[a] | Total recovery (%) |
|---|---|---|---|---|
| Mannan (%) | 11.7 | 6.6 ± 0.22; 56.6% | 2.4; 20.7% | 77.3 |
| Furfural (%)[c] |  | 0.1 ± 0.01; 2.0% | 0.1; 2.0% | 4.1 |
| HMF (%)[c] |  | 0.5 ± 0.00; 4.4% | 0.5; 4.2% | 8.6 |
| Acetic acid (%) |  | 3.25 ± 0.11; | 0.8; |  |

[a]The numbers after ";" is wt % of theoretical
[b]in oven dry (od) weight
[c]reported as of pentosan and hexosan for furfural and HMF, represent percent of pentosan and hexosan converted to furfural and HMF, respectively.

The total solids recovery was 94.5% with 74.2% in the unwashed solids fraction and 20% in the spent liquor hydrolysate as soluble and suspended solids. Overall recoveries of glucan, xylan, and mannan were 91.1, 69.4, and 77.3%, respectively. Glucan dissolution was minimal as 87.4% of the glucan was retained with the unwashed solids. Over two thirds of recovered xylan and mannan were present in the unwashed solids. Based on the analysis of a sample of washed pretreated solids, most of the recovered xylan and mannan were in the form of monomeric sugars, i.e., xylose and mannose, and less than 10% of them remained as polysaccharides. Approximately 50% of the furfural and HMF produced during pretreatment was found in the unwashed solids, while over 75% the acetic acid remained with the solids. This suggests that the unwashed solids contained more than the half of the dominant fermentation inhibitors.

Effect of Liquor Conditioning on Sugar and Inhibitor Profile

The liquor was concentrated through vacuum evaporation for high titer ethanol production by fermenting the combined the pretreatment spent liquor and enzymatic hydrolysate. And, the evaporation reduced inhibitor concentrations as shown by the difference between the measured and calculated inhibitor concentrations in the concentrated liquor (Table 8). The reduction in HMF concentration was minimal at about 15%. However, the reductions in furfural and acetic acid concentration were over 60% due to vaporization. Because about 50% of the furfural and HMF and 75% of the acetic acid were found in the unwashed solids, this translates to a net reduction of HMF, furfural and acetic acid of 8, 30, and 15%, respectively, when the solids and concentrated liquor were recombined. The reduction of 30% in furfural is not critical because furfural is a minor inhibitor from SPORL pretreatment of lodgepole pine with a concentration in the concentrated liquor of only 1.6 g/L. As such, evaporation did not significantly reduce inhibitors.

The low temperature evaporation did not degrade sugars in the pretreatment spent liquor hydrolysate. The differences between the measured and calculated sugar concentrations in the concentrated liquor were each within one standard deviation of 3%, except for mannose with 6% (Table 8).

Quasi-Simultaneous Enzymatic Saccharification and Combined Fermentation (qSSCombF)

The replicate fed-batch qSSCombF experiments were conducted for run 1, 2, and 5. The time-dependent ethanol concentration data show excellent repeatability.

Figure 20:
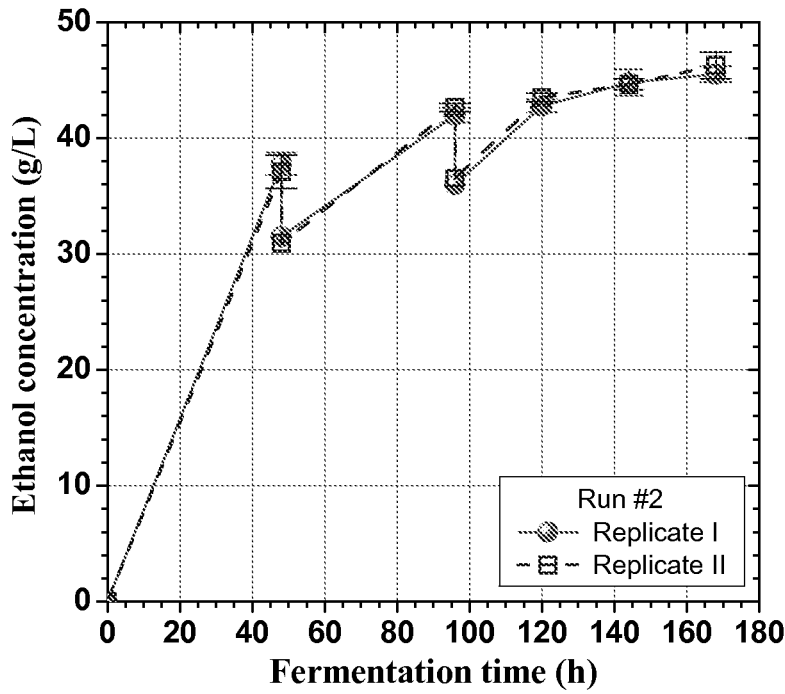
FIGS. 20A-20C show the results of a fed-batch quasi-simultaneous enzymatic saccharification with combined fermentation (qSSCombF), according to some embodiments.
Figure 20:
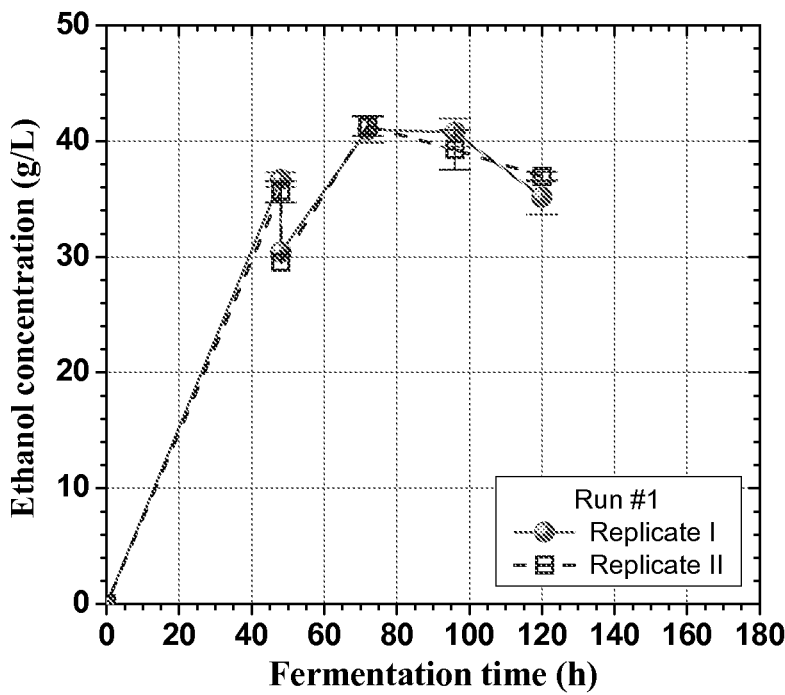
Figure 20:
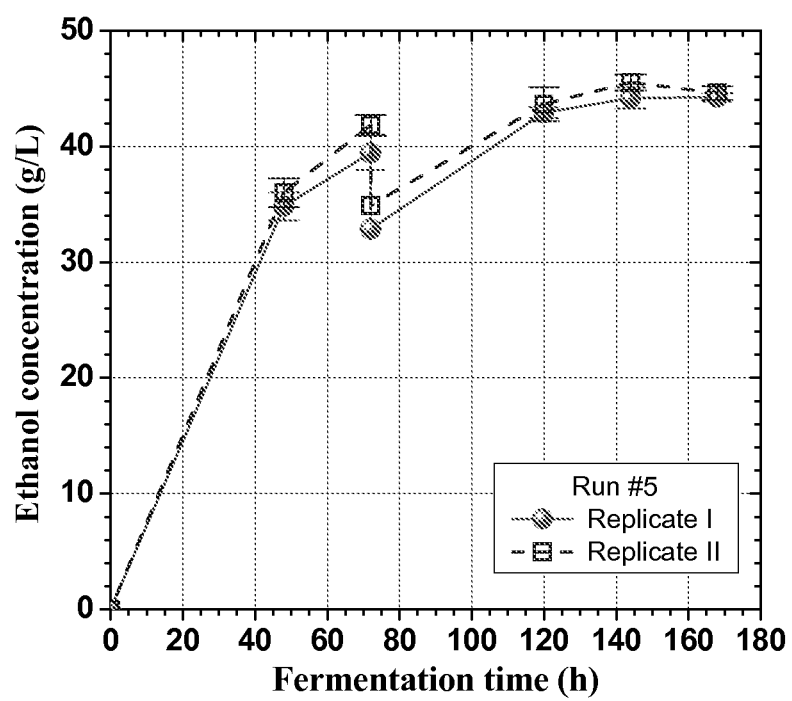

FIGS. 20A-20C show the results of a quasi-simultaneous enzymatic saccharification with combined fermentation (qSSCombF), according to some embodiments. FIG. 20A for run 2 shows excellent repeatability. Similar repeatability was shown for FIGS. 20B and 20C for runs 1 and 5, respectively. The differences in ethanol concentration were well within the ethanol measurement standard deviations based on duplicate analysis. The step decreases shown were from dilution when batch feeding wet solids. The time-dependent ethanol concentrations for the 7 runs are listed in Table 11 along with wet weight of the samples after batch feedings.

TABLE 11

| | Ethanol (g/L)[a]; Total fermentation broth wet weight (g) | | | | | Ethanol yield @ 48 h (g/g sugar)[b] | Maximal ethanol yield (g/g sugar)[b] | Maximal ethanol yield (L/ton wood) | Ethanol titer at maximal yield (g/L) |
|---|---|---|---|---|---|---|---|---|---|
| Run | 48 h | 72 h | 96 h | 120 h | 144 h | | | | |
| 1 | 36.1 ± 0.8<br>31 | 41.1 ± 1.0<br>37 | 40.0 ± 1.5<br>37 | | | 0.38<br>(75.1) | 0.40<br>(78.4) | 287 | 41.1 |
| 2 | 37.4 ± 1.2<br>31 | | 42.3 ± 0.5<br>37 | 43.1 ± 0.5<br>42 | 44.7 ± 0.8<br>42 | 0.38<br>(73.8) | 0.39<br>(76.6) | 280 | 45.9 |
| 3 | 34.9 ± 0.6<br>32.5 | 39.4 ± 0.6<br>32.5 | | | 42.8 ± 1.4<br>40 | 0.35<br>(67.6) | 0.38<br>(74.4) | 272 | 42.8 |
| 4 | 34.1 ± 1.2<br>34 | 39.9 ± 0.3<br>34 | 46.3 ± 0.8<br>34 | | 39.7 ± 1.3<br>43 | 0.33<br>(63.6) | 0.34<br>(66.4) | 243 | 39.7 |
| 5 | 35.4 ± 1.2<br>32 | 40.6 ± 1.2<br>32 | | 43.2 ± 1.0<br>38 | 44.9 ± 0.8<br>38 | 0.34<br>(65.8) | 0.39<br>(76.7) | 281 | 44.9 |
| 6 | 38.1 ± 1.5<br>33.5 | | 46.0 ± 0.9<br>33.5 | | 47.4 ± 0.6<br>41 | 0.35<br>(68.3) | 0.40<br>(77.9) | 285 | 47.4 |
| 7 | 38.6 ± 1.3<br>35 | | 46.7 ± 0.9<br>35 | | 45.1 ± 0.8<br>44 | 0.34<br>(67.1) | 0.37<br>(71.8) | 263 | 45.1 |

[a]sampled withdrawn before feeding further solids. Standard deviations were calculated from two HPLC determinations (four measurements for Run #1, #2, and #5 with replicate fermentation tests)
[b]based on the total of glucan, xylan, and mannan in the solids and glucose, xylose, and mannose in the pretreatment spent liquor hydrolysate. The numbers in the parenthesis are percent of theoretical (0.511 g/g sugar)

Ethanol titers of greater than 40 g/L were achieved for most of the runs after 96 hours of fermentation. Most of the runs achieved ethanol yields over 270 L/ton wood. Run #1 achieved the highest ethanol yield of 287 L/ton wood with a saccharification and fermentation yield of 78.4% of theoretical, with an ethanol concentration of 41.1 g/L. Run #1 has the lowest final total solids loading of 16.7% which facilitated insoluble solids liquefaction and saccharification. When comparing Run #2 with #4, the final total solids are almost the same but the solids were fed into the reactor differently, i.e., Run #2 was fed with smaller doses of 1.42 g three times while Run #4 was fed larger doses of 2.12 g two times.

Frequent feeding of a smaller amount (Run #2) produced better liquefaction which resulted in a higher ethanol yield of 280 L/ton wood and saccharification and fermentation yield of 76.5% of theoretical. This is in comparison to 243 L/ton wood or 66.7% of theoretical from Run #4 were biomass was fed less often at higher doses. The difference in inhibitor concentrations between the two runs does not appear to explain this discrepancy (discussed below). The observed differences between Run #2 and #4 were caused by the difference in the rate of solids liquefaction and saccharification. To further illustrate this point, compare Run #6 with #7. Both were fed two times. However, Run #6 was fed 1.77 g each time while Run #7 was fed 2.12 g each time. Despite Run #6 total solids loading of 19.5% being slightly lower than 20.1% for Run #7, Run #6 produced higher ethanol yield of 285 L/ton wood (78.4% of theoretical) at higher titer of 47.4 g/L than Run #7 with 263 L/ton wood (71.8% of theoretical) at 45.1 g/L. Similar comparisons can be made between Run #3 and #5 where Run #5 was fed 1.42 g each time while Run #3 was fed 1.77 g each time. The final total solids loadings were almost the same for the two runs. However, Run #5 produced a higher ethanol yield of 281 L/ton wood (76.7% of theoretical) at a higher titer of 44.9 g/L than the 272 L/ton (74.4% of theoretical) at 42.8 g/L from Run #3.

Figure 21:
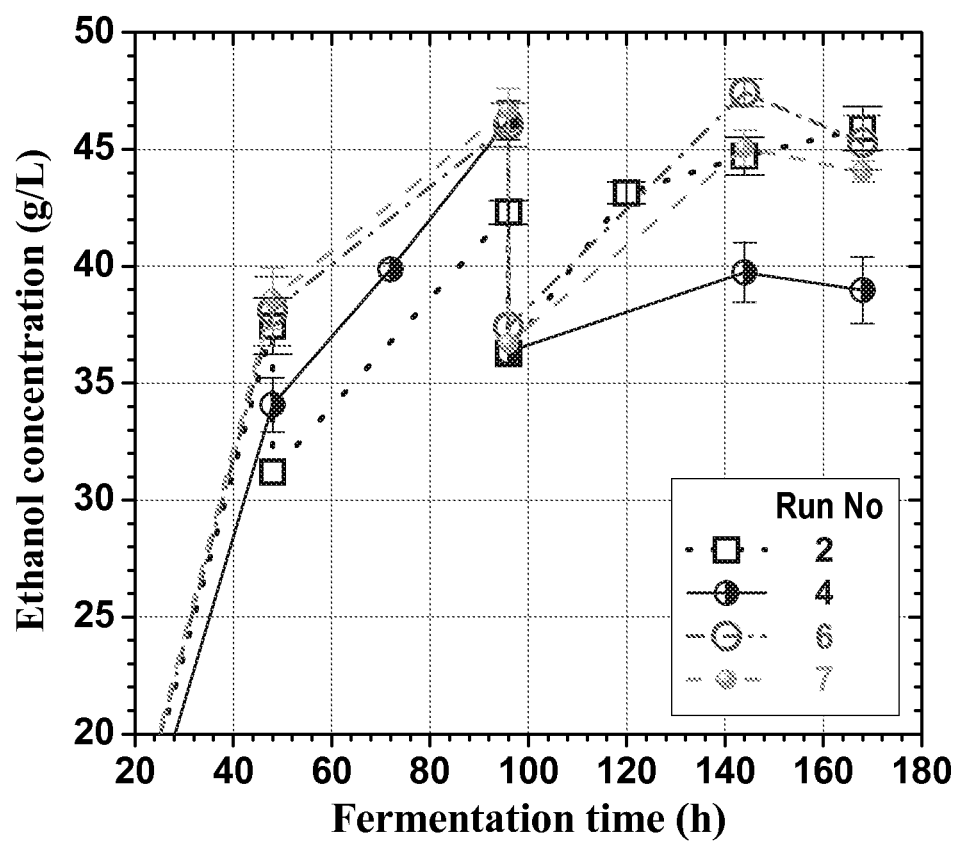
FIG. 21 illustrates the effectiveness of the use of a lignosulfonate additive and a pH of 5.5 to provides a high titer and high yield ethanol production process, according to some embodiments.

FIG. 21 illustrates the effectiveness of the use of a lignosulfonate additive and a pH of 5.5 to a high titer and high yield ethanol production process, according to some embodiments. A high ethanol yield of 285 L (75 gallon)/ton wood at a high titer of 47.4 g/L was produced, very high yield relative to the state-of-the-art processes that do not include a lignosulfonate additive and/or a pH of greater than 4.8. The process can include, for example, applying a SPORL pretreatment spent liquor hydrolysate containing a lignosulfonate to an enzymatic saccharification of a SPORL pretreated dewatered lignocellulose at an elevated pH of 5.5 or higher.

One of skill will appreciate that the enablement of the teachings extends well-beyond the scope of the examples. For at least this reason, equivalents are intended to be encompassed by the following claims. Moreover, there are numerous lists and Markush groups taught and claimed herein. One of skill will appreciate that each such list and group contains various species and can be modified by the removal, or addition, of one or more of species, since every list and group taught and claimed herein may not be applicable to every embodiment feasible. As such, components in such lists can be removed, and may expected to be removed, in some embodiments. Each document referenced herein has been buyer selected for incorporation of either essential or non-essential matter for purposes of ensuring all legal requirements are met in this teaching. All references to publications, patents, patent applications, and non-patent literature mentioned are herein incorporated by reference into the specification to the same extent as if each was specifically indicated to be herein incorporated by reference in its entirety.

I claim:

1. A system for reducing non-specific enzyme binding to enhance processing of a lignocellulosic material, the system comprising:
a reaction vessel;
a lignocellulosic feedstock comprising a component selected from the group consisting of a hardwood, a softwood, and a non-wood material;
an enzyme component including a cellulase, a hemicellulase, or a combination thereof;
a lignosulfonate additive selected from the group consisting of a hardwood lignosulfonate, a softwood lignosulfonate, and a non-wood lignosulfonate; and,
water;
wherein,
the pH of the lignosulfonate additive ranges from 4.8 to 6.2, and the lignosulfonate additive is added to the system at the enzymatic hydrolysis step of the processing; and,
the reaction vessel contains a combination of the lignocellulosic feedstock, the water, and the enzyme component at a pH ranging from about 5.2 to about 6.2.

2. The system of claim 1, wherein the lignosulfonate additive is a softwood sulfite lignosulfonate.

3. The system of claim 1, further comprising a pretreatment vessel for pretreating the lignocellulosic feedstock, the pretreatment vessel containing an aqueous solution of sulfite or bisulfite at a pH ranging from about 1.0 to about 5.

4. The system of claim 1, further comprising a fermentation vessel containing a yeast for fermenting the saccharified lignocellulosic feedstock.

5. The system of claim 1, wherein the enzyme component comprises *Trichoderma reesei*.

6. A method for reducing non-specific binding to enhance processing of a lignocellulosic material, the method comprising:
obtaining the system of claim 1;
adding the lignosulfonate additive to the system at a pH ranging from 4.8 to 6.2 at the enzymatic hydrolysis step of the processing;
and,
reacting the combination of the lignocellulosic feedstock, the lignosulfonate additive, the water, and the enzyme component at the pH ranging from about 5.2 to about 6.2 during the enzymatic hydrolysis step of the processing.

7. The method of claim 6, wherein the lignosulfonate is a softwood sulfite lignosulfonate.

8. The method of claim 6, further comprising pretreating the lignocellulosic feedstock in a pretreatment vessel containing an aqueous solution of sulfite or bisulfite at a pH ranging from about 1.0 to about 5.

9. The method of claim 6, further comprising fermenting the saccharified lignocellulosic feedstock in a fermentation vessel containing a yeast.

10. The method of claim 6, wherein the enzyme component comprises *Trichoderma reesei*.

11. A system for enhancing enzymatic saccharification of cellulose, the system comprising:
a reaction vessel;
a lignocellulosic feedstock comprising a component selected from the group consisting of a hardwood, a softwood, and a non-wood material, with the proviso that the feedstock does not contain a lignosulfonate;
an enzyme component including a cellulase, a hemicellulase, or a combination thereof;
a lignosulfonate additive selected from the group consisting of a hardwood lignosulfonate, a softwood lignosulfonate, and a non-wood lignosulfonate; and,
water;

wherein,
the pH of the lignosulfonate additive ranges from 4.8 to 6.2, and the lignosulfonate additive is added to the system at the enzymatic hydrolysis step of the processing;
the reaction vessel contains a combination of the lignocellulosic feedstock, the water, the enzyme component, and the lignosulfonate additive during the enzymatic hydrolysis step of the processing; and,
the lignocellulosic feedstock is saccharified in the reaction vessel for fermentation.

12. The system of claim 11, wherein the reaction vessel contains the combination of the lignocellulosic feedstock, the water, and the enzyme component at a pH ranging from about 5.2 to about 6.2.

13. The system of claim 11, further comprising a pretreatment vessel for pretreating the lignocellulosic feedstock, the pretreatment vessel containing an aqueous solution of sulfite or bisulfite at a pH ranging from about 1.0 to about 5.

14. The system of claim 11, further comprising a fermentation vessel containing a yeast for fermenting the saccharified lignocellulosic feedstock.

15. The system of claim 11, wherein the enzyme component comprises *Trichoderma reesei*.

16. A method for enhancing enzymatic saccharification of polysaccharides, the method comprising:
obtaining the system of claim 11;
adding the lignosulfonate additive to the system at a pH ranging from 4.8 to 6.2 at the enzymatic hydrolysis step of the processing; and,
reacting the combination of the lignocellulosic feedstock, the water, the enzyme component, and the lignosulfonate additive at the pH ranging from about 5.2 to about 6.2 to saccharify the lignocellulosic feedstock during the enzymatic hydrolysis step of the processing.

17. The method of claim 16, wherein the reacting occurs at a pH ranging from about 5.5 to about 6.0.

18. The method of claim 16, further comprising pretreating the lignocellulosic feedstock in a pretreatment vessel containing an aqueous solution of sulfite or bisulfite at a pH ranging from about 1.0 to about 5.

19. The method of claim 16, further comprising fermenting the saccharified lignocellulosic feedstock in a fermentation vessel containing a yeast.

20. The method of claim 16, wherein the enzyme component comprises *Trichoderma reesei*.

21. A system for producing a biofuel, the system comprising:
a pretreatment vessel containing an aqueous solution of sulfite or bisulfite at a pH ranging from about 1.0 to about 5;
a reaction vessel;
a lignocellulosic feedstock comprising a component selected from the group consisting of a hardwood, a softwood, and a non-wood material;
an enzyme component comprising *Trichoderma reesei*;
a lignosulfonate additive selected from the group consisting of a hardwood lignosulfonate, a softwood lignosulfonate, and a non-wood lignosulfonate;
water; and,
a fermentation vessel containing a yeast for fermenting the saccharified lignocellulosic feedstock;
wherein,
the pH of the lignosulfonate additive ranges from 4.8 to 6.2, and the lignosulfonate additive is added to the system at the enzymatic hydrolysis step of the processing;
the reaction vessel contains the combination of the lignocellulosic feedstock, the water, the enzyme component, and the lignosulfonate at a pH ranging from about 5.2 to about 6.2 during the enzymatic hydrolysis step of the processing;
the lignocellulosic feedstock is saccharified in the reaction vessel for fermentation; and,
the saccharified lignocellulosic feedstock is converted to ethanol in the fermentation vessel.

22. A method of producing a biofuel, the method comprising:
obtaining the system of claim 21;
pretreating the lignocellulosic feedstock in the pretreatment vessel;
adding the lignosulfonate additive to the system at a pH ranging from 4.8 to 6.2 at the enzymatic hydrolysis step of the processing;
reacting the combination of the lignocellulosic feedstock, the water, the enzyme component, and the lignosulfonate at the pH ranging from about 5.2 to about 6.2 to saccharify the lignocellulosic feedstock during the enzymatic hydrolysis step of the processing; and,
fermenting the saccharified lignocellulosic feedstock to create a biofuel.

* * * * *